United States Patent
Quin et al.

(10) Patent No.: US 9,228,870 B2
(45) Date of Patent: *Jan. 5, 2016

(54) ULTRASONIC FLOWMETER HAVING PRESSURE BALANCING SYSTEM FOR HIGH PRESSURE OPERATION

(71) Applicant: Cameron International Corporation, Houston, TX (US)

(72) Inventors: David Francis Anthony Quin, Limerick (IE); Kevin Peter Minnock, Longford (IE); Francis Anthony O'Brien, Cork (IE); Finian McCarthy, Longford (IE)

(73) Assignee: Cameron International Corporation, Houston, TX (US)

( * ) Notice: Subject to any disclaimer, the term of this patent is extended or adjusted under 35 U.S.C. 154(b) by 214 days.

This patent is subject to a terminal disclaimer.

(21) Appl. No.: 13/975,235

(22) Filed: Aug. 23, 2013

(65) Prior Publication Data

US 2014/0053659 A1 Feb. 27, 2014

Related U.S. Application Data

(63) Continuation of application No. 13/106,782, filed on May 12, 2011, now Pat. No. 8,522,623.

(60) Provisional application No. 61/448,629, filed on Mar. 2, 2011.

(51) Int. Cl.
*G01F 1/66* (2006.01)
*G01N 29/024* (2006.01)
*G01F 15/10* (2006.01)
*G01F 15/14* (2006.01)

(52) U.S. Cl.
CPC ............ *G01F 1/662* (2013.01); *G01F 1/667* (2013.01); *G01F 15/10* (2013.01); *G01F 15/14* (2013.01); *G01N 29/024* (2013.01); *G01N 2291/02836* (2013.01); *G01N 2291/2634* (2013.01)

(58) Field of Classification Search
CPC ........................................................ G01F 1/66
USPC ........................................ 73/861.28, 861.27
See application file for complete search history.

(56) References Cited

U.S. PATENT DOCUMENTS

| | | |
|---|---|---|
| 4,003,252 A | 1/1977 | Dewath |
| 4,173,889 A | 11/1979 | Forster et al. |
| 4,315,523 A | 2/1982 | Mahawili et al. |

(Continued)

FOREIGN PATENT DOCUMENTS

| | | |
|---|---|---|
| EP | 0952430 A1 | 10/1999 |
| FR | 2911680 A1 | 7/2008 |

(Continued)

OTHER PUBLICATIONS

PCT Search Report and Written Opinion for PCT/US2012/025723, mailed on May 18, 2012.

(Continued)

*Primary Examiner* — Jewel V Thompson
(74) *Attorney, Agent, or Firm* — Fletcher Yoder P.C.

(57) ABSTRACT

A system is provided with an ultrasonic flow meter. The ultrasonic flow meter includes a first ultrasonic transducer disposed about a fluid flow path, and a pressure balancing system configured to pressure balance the first ultrasonic transducer relative to a fluid flow along the fluid flow path.

28 Claims, 11 Drawing Sheets

(56) References Cited

U.S. PATENT DOCUMENTS

| | | |
|---|---|---|
| 4,391,150 A | 7/1983 | Rey |
| 5,194,012 A | 3/1993 | Cairns |
| 5,477,101 A | 12/1995 | Ounadjela |
| 5,558,532 A | 9/1996 | Hopper |
| 5,794,701 A | 8/1998 | Cunningham et al. |
| 5,841,734 A | 11/1998 | Ritter et al. |
| 6,354,146 B1 | 3/2002 | Birchak et al. |
| 6,418,792 B1 | 7/2002 | Spychalski |
| 6,429,926 B1 | 8/2002 | Williamson et al. |
| 6,481,504 B1 | 11/2002 | Gatherar |
| 6,644,119 B1 | 11/2003 | Sinha |
| 6,823,941 B2 | 11/2004 | Donald |
| 6,851,444 B1 | 2/2005 | Kohl et al. |
| 7,234,524 B2 | 6/2007 | Shaw et al. |
| 7,243,729 B2 | 7/2007 | Tyrrell et al. |
| 7,380,835 B2 | 6/2008 | McCoy et al. |
| 7,389,786 B2 | 6/2008 | Zeck |
| 7,389,787 B2 | 6/2008 | Means et al. |
| 8,066,076 B2 | 11/2011 | Donald et al. |
| 8,327,875 B2 | 12/2012 | Grace et al. |
| 8,522,623 B2 * | 9/2013 | Quin et al. ............... 73/861.28 |
| 8,522,624 B2 | 9/2013 | Quin et al. |
| 8,763,693 B2 | 7/2014 | McHugh |
| 8,997,848 B2 | 4/2015 | Quin |
| 9,062,527 B2 | 6/2015 | McHugh |
| 2002/0089659 A1 | 7/2001 | Williamson et al. |
| 2002/0011336 A1 | 1/2002 | Baskett et al. |
| 2004/0226360 A1 | 11/2004 | Lotters |
| 2008/0148841 A1 | 6/2008 | Sakai |
| 2008/0163692 A1 | 7/2008 | Huang et al. |
| 2008/0217022 A1 | 9/2008 | Deans |
| 2008/0257032 A1 | 10/2008 | Zollo et al. |
| 2009/0025936 A1 | 1/2009 | Donald et al. |
| 2010/0126600 A1 | 5/2010 | Watson |
| 2012/0312522 A1 | 12/2012 | Quin et al. |

FOREIGN PATENT DOCUMENTS

| | | |
|---|---|---|
| GB | 2163557 A1 | 2/1986 |
| WO | WO0019242 | 4/2000 |
| WO | WO0020829 | 4/2000 |
| WO | WO2008095113 A2 | 8/2008 |
| WO | 20100065210 A1 | 6/2010 |

OTHER PUBLICATIONS

U.S. Appl. No. 14/726,962, filed Jun. 1, 2015, David Francis Anthony Quin.

U.S. Appl. No. 14/726,523, filed May 30, 2015, Edmund Peter McHugh.

* cited by examiner

ULTRASONIC FLOWMETER HAVING PRESSURE BALANCING SYSTEM FOR HIGH PRESSURE OPERATION

CROSS REFERENCE TO RELATED APPLICATIONS

This application claims priority to U.S. Non-Provisional patent application Ser. No. 13/106,782, entitled "Ultrasonic Flowmeter Having Pressure Balancing System for High Pressure Operation", filed on May 12, 2011, which is herein incorporated by reference in its entirety, and which claims priority to and benefit of U.S. Provisional Patent Application No. 61/448,629, entitled "Ultrasonic Flowmeter Having Pressure Balancing System for High Pressure Operation", filed Mar. 2, 2011, which is herein incorporated by reference in its entirety.

FIELD OF THE INVENTION

The present invention relates to chemical-injection management systems. More particularly, the present invention relates to high-pressure chemical-injection management systems that can measure low flow rates.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Wells are often used to access resources below the surface of the earth. For instance, oil, natural gas, and water are often extracted via a well. Some wells are used to inject materials below the surface of the earth, e.g., to sequester carbon dioxide, to store natural gas for later use, or to inject steam or other substances near an oil well to enhance recovery. Due to the value of these subsurface resources, wells are often drilled at great expense, and great care is typically taken to extend their useful life.

Chemical-injection management systems are often used to maintain a well and/or enhance throughput of a well. For example, chemical-injection management systems are used to inject corrosion-inhibiting materials, foam-inhibiting materials, wax-inhibiting materials, and/or antifreeze to extend the life of a well or increase the rate at which resources are extracted from a well. Typically, these materials are injected into the well in a controlled manner over a period of time by the chemical-injection management system using a flow meter. Unfortunately, existing flow meters are unable to provide accurate measurements at high pressures and low flow rates.

BRIEF DESCRIPTION OF THE DRAWINGS

These and other features, aspects, and advantages of the present invention will become better understood when the following detailed description of certain exemplary embodiments is read with reference to the accompanying drawings in which like characters represent like parts throughout the drawings, wherein.

DETAILED DESCRIPTION OF SPECIFIC EMBODIMENTS

Figure 1:
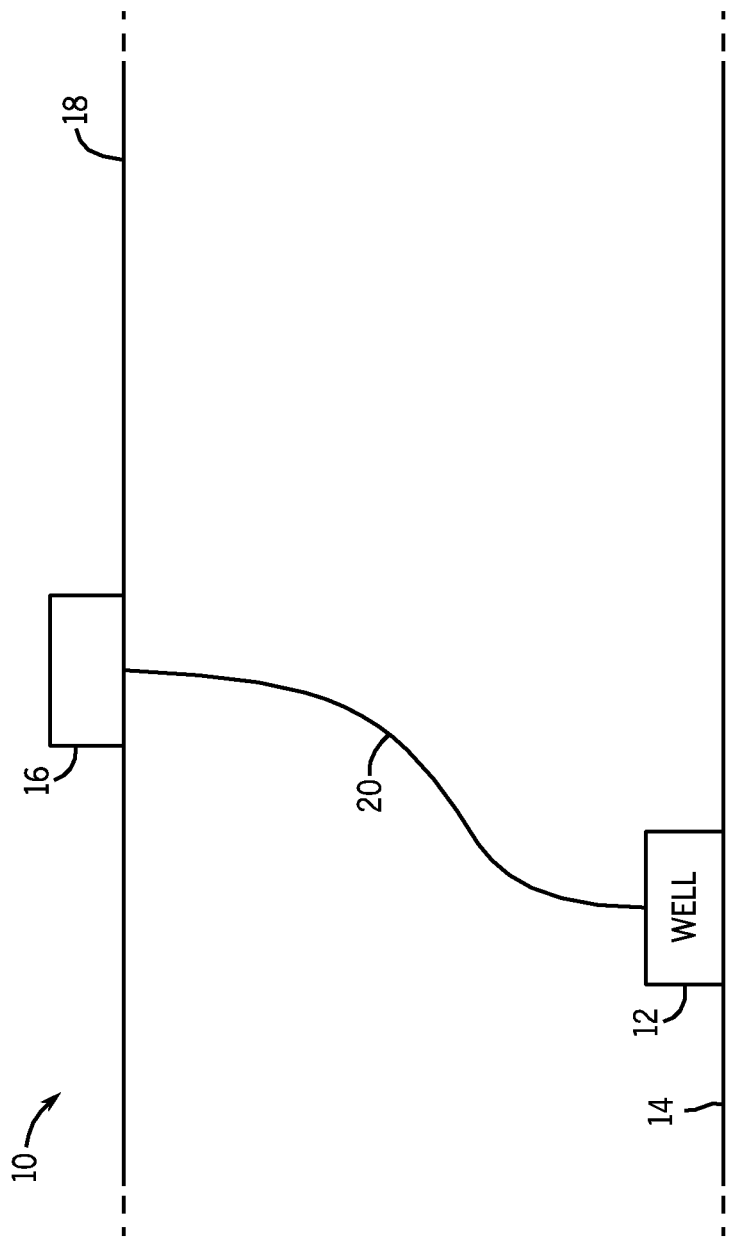
FIG. 1 is a block diagram of an embodiment of an exemplary resource extraction system.

One or more specific embodiments of the present invention will be described below. These described embodiments are only exemplary of the present invention. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Moreover, the use of "top," "bottom," "above," "below," and variations of these terms is made for convenience, but does not require any particular orientation of the components.

Certain exemplary embodiments of the present invention a low flow ultrasonic flow meter capable of measuring low flow rates, while operating under high-pressure conditions. In certain embodiments, the low flow ultrasonic flow meter may be used with, coupled to, or generally associated with underwater equipment, such as subsea equipment, in a variety of applications. For example, embodiments of the low flow ultrasonic flow meter may be used with, coupled to, or generally associated with mineral extraction equipment, flow control equipment, pipelines, and the like. In one embodiment, as discussed in detail below, the low flow ultrasonic flow meter may be used with, coupled to, or generally associated a chemical-injection management system. However, the foregoing examples are not intended to be limiting.

In certain embodiments, the low flow ultrasonic flow meter may be designed to operate with pressures ranging between approximately 0 to 50,000 psi, while the flow rates may range between approximately 0.01 to 1000 liters/hour. For example, the flow meter may be configured to measure low flow rates less than approximately 0.01, 0.02, 0.03, 0.04, 0.05, 0.1, 0.2, 0.3, 0.4, 0.5, 0.6, 0.7, 0.8, 0.9, 1, 2, 3, 4, 5, 10, 15, 20, or 25 liters/hour, while operating under pressures up to or greater than 5,000 psi, 10,000 psi, 15,000 psi, 20,000 psi, 25,000 psi, 30,000 psi, 40,000 psi, or 50,000 psi. However, the disclosed embodiments are not limited to any specific operating ranges, and the disclosed ranges are intended to be non-limiting examples.

Ultrasonic transducers in combination with acoustic damping allow the flow meter to measure the low chemical flow rates in the chemical-injection management system. In certain embodiments, the ultrasonic transducers rapidly switch back and forth between acting as an actuator to produce ultrasonic waves, and acting as a sensor to detect ultrasonic waves. For example, an upstream transducer sends signals downstream through the chemical fluid to a downstream transducer, while the downstream transducer sends signals upstream through the chemical fluid to the upstream transducer. The time required by the signals to reach the opposing transducer determines the flow rate of the chemical fluid through the chemical injection management system.

As discussed in detail below, the accuracy of the transducers depends on the acoustic isolation of the transducers from acoustic noise, which can interfere with the communication through the chemical fluid between the transducers. For example, the transducers may be covered in polyether ether ketone (PEEK) in combination with a PEEK acoustic isolator to block acoustic noise and communication between the transducers outside of the chemical fluid. In some embodiments, the conduit carrying the chemical fluid may be covered in PEEK in combination with PEEK covered transducers to block acoustic noise and communication outside of the chemical fluid. In some embodiments, a chamber may surround the conduit, house the transducers, and provide acoustic damping. For example, the chamber may be filled with an acoustic damping material, such as a fluid, particles, structures, or a combination thereof.

The flow meter may also include a pressure balancing system that permits operation of the flow meter at high pressures. For example, the pressure balancing system may include the chamber around the conduit, wherein the chamber includes the transducers and is pressure balanced with the conduit. In certain embodiments, the conduit and the chamber may be in fluid communication with one another. The equalization of the pressure in the conduit and chamber prevents damage to the ultrasonic transducers. In other embodiments, a pressure adjusting/balancing mechanism may be disposed at an interface between the chamber and the conduit, thereby enabling pressure balancing between the conduit and the chamber. For example, the pressure adjusting/balancing mechanism may include a bellows, a balloon, a diaphragm, a piston-cylinder assembly, gel slugs in biros, or any combination thereof. For example, the bellows, balloon, or diaphragm may be made of an expandable/compressible material, such as an elastomer. As the chemical fluid changes pressure, the pressure adjusting/balancing mechanism moves (e.g., expands and contracts) maintaining a pressure equilibrium between the conduit and the chamber. However, in certain embodiments, the pressure adjusting/balancing mechanism may include a variety of movable elements, which are configured to balance fluid pressure internal and external to the conduit by moving the element in response to a pressure differential between the chamber and the conduit. In this manner, the pressure adjusting/balancing mechanism reduces stress on the conduit, thereby protecting the ultrasonic transducers coupled to the conduit over a wide range of pressures. Although the disclosed embodiments are presented in context of an ultrasonic flow meter, the disclosed embodiments may be used with any type of flow meters using various sensors or transducers coupled to the conduit.

FIG. 1 depicts an exemplary sub-sea resource extraction system 10. In particular, the sub-sea resource extraction system 10 may be used to extract oil, natural gas, and other related resources from a well 12, located on a sub-sea floor 14, to an extraction point 16 at a surface location 18. The extraction point 16 may be an on-shore processing facility, an off-shore rig, or any other extraction point. The sub-sea resource extraction system 10 may also be used to inject fluids, such as chemicals, steam, and so forth, into the well 12. These injected fluids may aid the extraction of resources from the well 12.

As sub-sea resource extraction systems 10 become more complex, reach greater depths, extend to greater offshore distances, and operate at higher pressures, the auxiliary equipment which supply working fluids to these sub-sea resource extraction systems 10 increase in complexity as well. The working fluids may be supplied to the sub-sea equipment using flexible jumper or umbilical lines 20. The systems may be comprised of reinforced polymer and small diameter steel supply lines, which are interstitially spaced into a larger reinforced polymer liner. As the working pressure of the sub-sea equipment increases, the supply pressures and injection pressures also increase.

Figure 2:
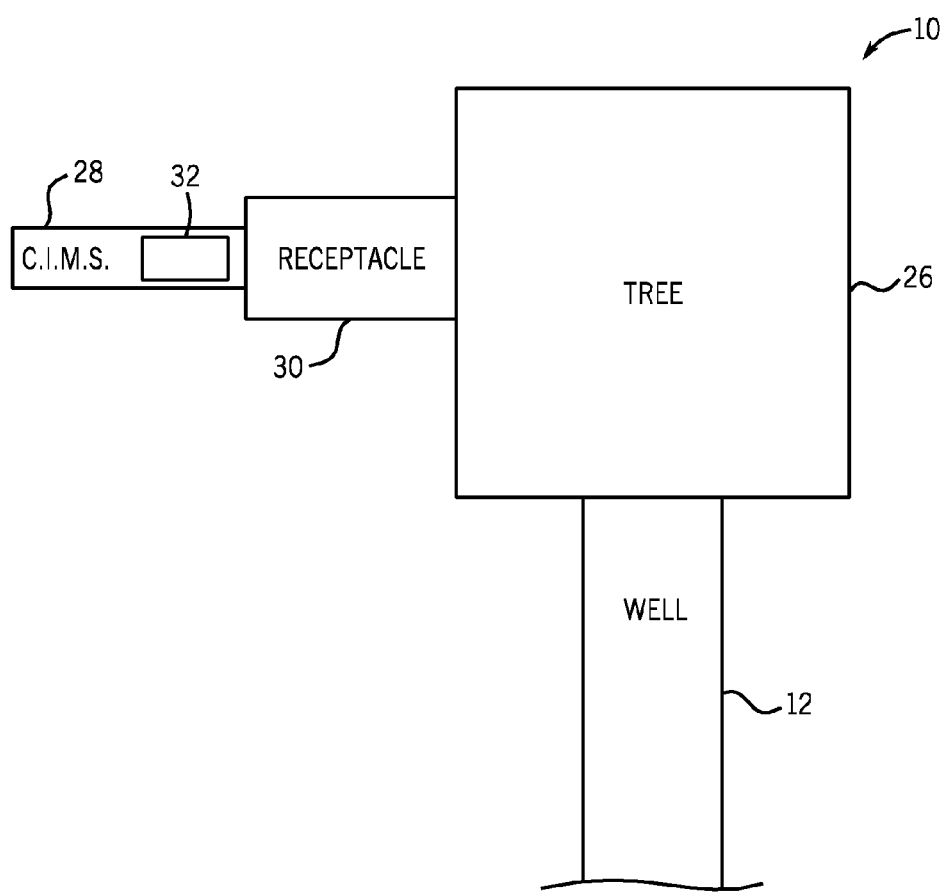
FIG. 2 is a block diagram of an embodiment of an exemplary resource extraction system with a chemical injection management system.

FIG. 2 depicts an exemplary resource extraction system 10, which may include a well 12, colloquially referred to as a "Christmas tree" 26 (hereinafter, a "tree"), a chemical-injection management system (C.I.M.S.) 28, and a valve receptacle 30. The illustrated resource extraction system 10 may be configured to extract hydrocarbons (e.g., oil and/or natural gas). When assembled, the tree 26 may couple to the well 12 and include a variety of valves, fittings, and controls for operating the well 12. The chemical-injection management system 28 may be coupled to the tree 26 via the valve receptacle 30. The tree 26 may permit fluid communication between the chemical-injection management system 28 and the well 12. As explained below, the chemical-injection management system 28 may be configured to regulate the flow of a chemical through the tree 26 and into the well 12 through use of a flow regulator 32.

Figure 3:
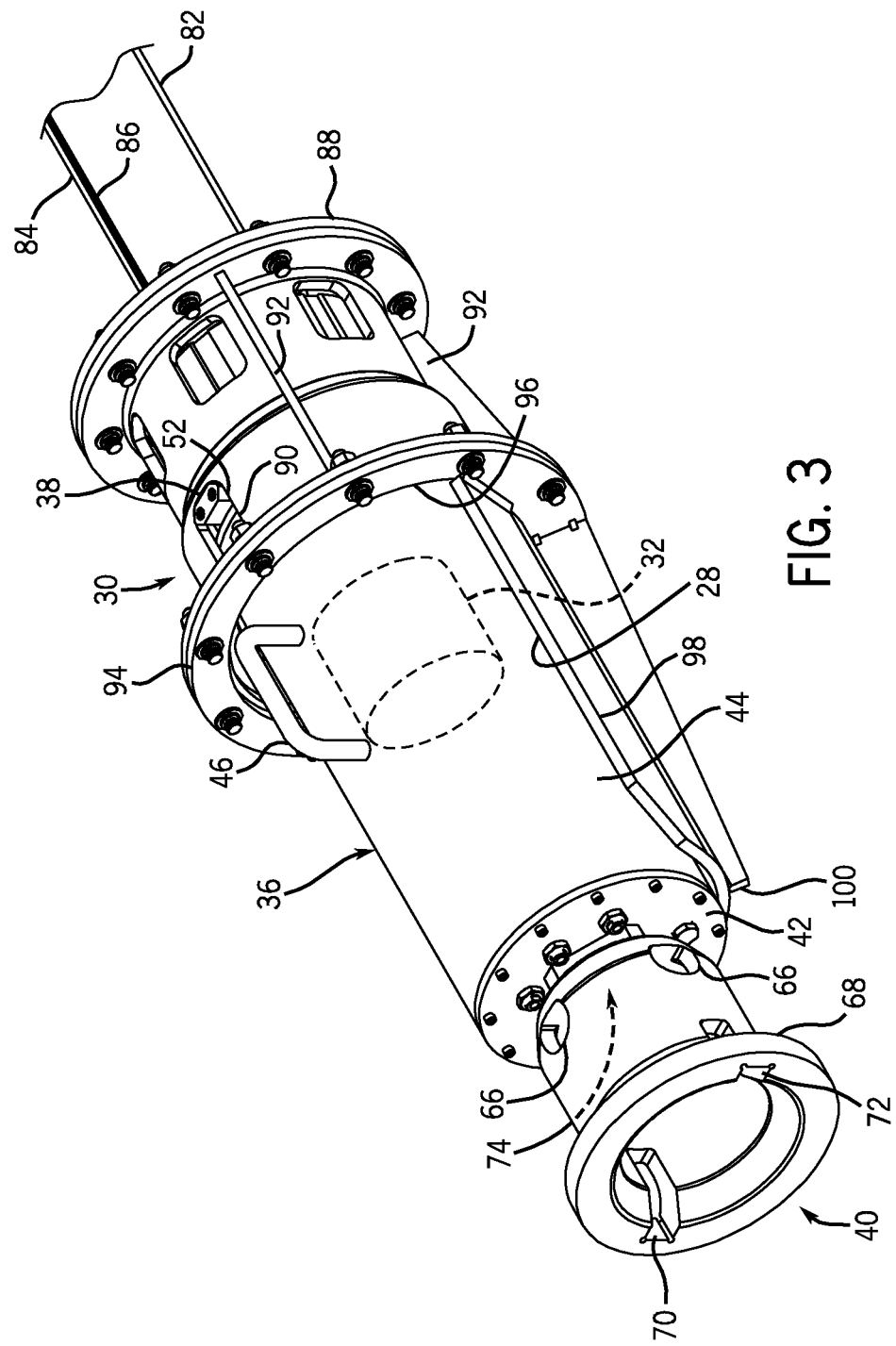
FIG. 3 is a partial perspective view of an embodiment of the chemical-injection management system of FIG. 2.

FIG. 3 is a perspective view of the chemical-injection management system 28, mated with the valve receptacle 30. As illustrated, the chemical-injection management system 28 may include the flow regulator 32, a housing 36, a tree interface 38, key 52, and an ROV (remotely operated vehicle) interface 40. The housing 36 may include an outer-end plate 42, a sidewall 44, a handle 46, and an inner-end plate. The sidewall 44 and end plates 42 may be made from a generally rigid, corrosion-resistant material and may generally define a right cylindrical volume with a circular base. The handle 46 may be affixed (for example, welded) to the sidewall 44 and may have a U-shape. The tree interface 38 allows connection of the chemical-injection management system 28 to the tree 26 via complementary components on the valve receptacle 30.

The illustrated ROV interface 40 may include apertures 66, a flared grip 68, slots 70 and 72, and a torque-tool interface 74. In some embodiments, the ROV interface 40 may be an API 17D class 4 ROV interface. The ROV interface 40 may be attached to the outer-end plate 42. The torque-tool interface 74, which may be configured to couple to a torque tool on an ROV, may be disposed within the flared grip 68 and generally symmetrically between the slots 70 and 72. The torque-tool interface 74 may be coupled to an internal drive mechanism to carry out the commands of the ROV.

Valve receptacle 30 may include a fluid inlet 82, a fluid outlet 84, an electrical connection 86, a mounting flange 88, a keyway 90, support flanges 92, an outer flange 94, a valve aperture 96, a valve tray 98, and tray supports 100. The fluid inlet 82 may be a fluid conduit, tube, or conduit that fluidly communicates with a fluid source, such as a supply of a liquid to be injected, and the fluid outlet 84 may be a fluid conduit, tube, or conduit that is in fluid communication with the well 12. The electrical connection 86 may couple to a power source, a user input device, a display, and/or a system controller. The mounting flange 88 may be configured to couple the valve receptacle 30 to the tree 26. The keyway 90 and the valve tray 98 may be configured to at least roughly align the chemical-injection management system 28 to the valve receptacle 30 during an installation of the chemical-injection management system 28. Specifically, the valve tray 98 may be configured to support the chemical-injection management system 28 as it slides into the valve aperture 96, and the key 52 may be configured to slide into the keyway 90 to rotationally position the chemical-injection management system 28.

Figure 4:
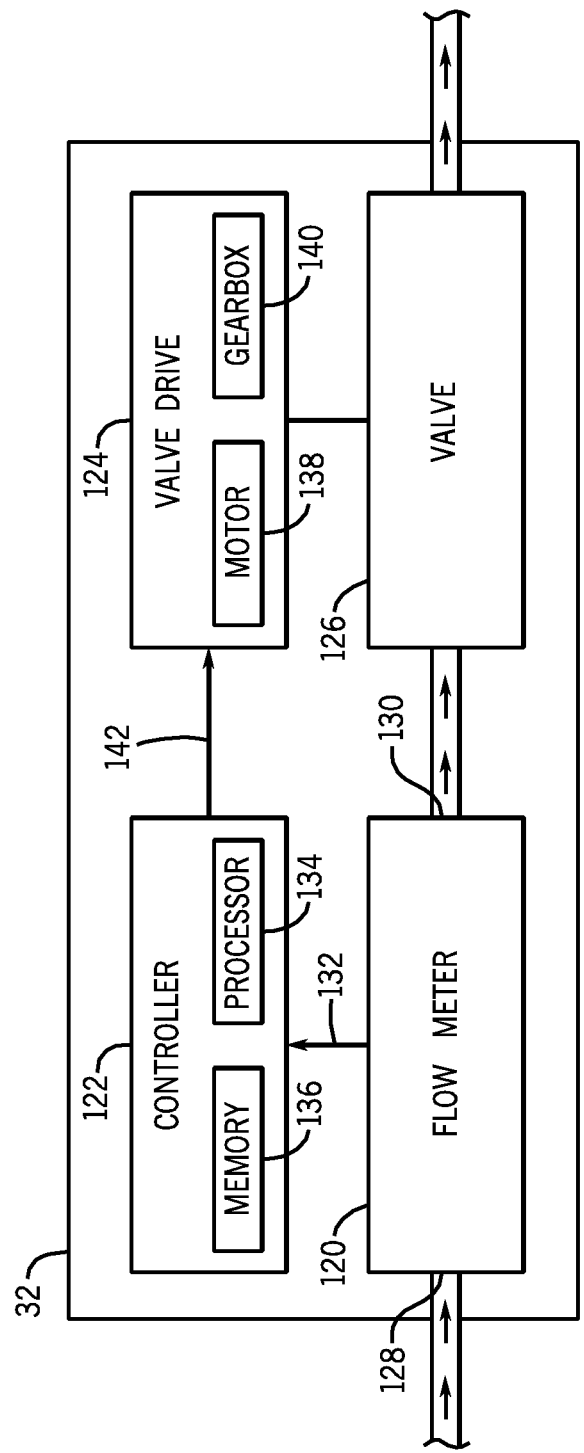
FIG. 4 is a block diagram of an embodiment of the flow regulator in FIG. 3 with a low flow ultrasonic flow meter.

FIG. 4 is a block diagram of an embodiment of the flow regulator 32 in FIG. 3 with a low flow ultrasonic flow meter 120. As discussed in detail below, the flow meter 120 may include an acoustic isolation system and a pressure balancing system configured to improve performance and operability of the flow meter 120 over a greater range of pressures and flow rates. In addition to the flow meter 120, the flow regulator includes a controller 122, valve drive 124, and valve 126. As discussed below, the flow regulator 32 may be configured to regulate or control a flow parameter, such as a volumetric flow rate, a mass flow rate, a volume, and/or a mass of fluid flowing to or from the well 12. The flow meter 120 may include a fluid inlet 128, a fluid outlet 130, and a measurement signal path 132. The measurement signal path 132 provides signal data to the controller 122 for processing.

The controller 122 may include a processor 134 and memory 136. The controller 122 may be configured to determine a volumetric flow rate, a mass flow rate, a volume, or a mass based on a signal from the flow meter 120. The controller 122 may also be configured to regulate or control one or more of these parameters based on the signal from the flow meter 120 by signaling the valve drive 124 to adjust the valve 126. To this end, the controller 122 may include software and/or circuitry configured to execute a control routine. In some embodiments, the control routine and/or data based on a signal from the flow meter 120 may be stored in memory 136 or another computer-readable medium.

The illustrated valve drive 124 may include a motor 138, a gearbox 140, and a control signal path 142 to the controller 122. In operation, the controller 122 may exercise feedback control over fluid flow. The controller 122 may transmit a control signal 142 to the valve drive 124. The content of the control signal 142 may be determined by, or based on, a comparison between a flow parameter (e.g., a volumetric flow rate, a mass flow rate, a volume, or a mass) measured by the flow meter 120 and a desired value of the flow parameter. For instance, if the controller 122 determines that the flow rate through the flow regulator 32 is less than a desired flow rate, the controller 122 may signal 142 the valve drive 124 to open valve 126 some distance. In response, the motor 138 may drive the gearbox 140, and the gearbox 140 may convert rotational movement from the motor 138 into linear translation of the valve 126, or rotation of the valve 126. As a result, in some embodiments, the flow rate through the valve 126 may increase as the valve opens. Alternatively, if the controller 122 determines that the flow rate (or other flow parameter) through the flow regulator 32 is greater than a desired flow rate (or other flow parameter), the controller 122 may signal 142 the valve drive 124 to close the valve 126 some distance, thereby potentially decreasing the flow rate. In other words, the controller 122 may signal the valve drive 124 to open or close the valve 126 some distance based on a flow parameter sensed by the flow meter 120.

Figure 5:
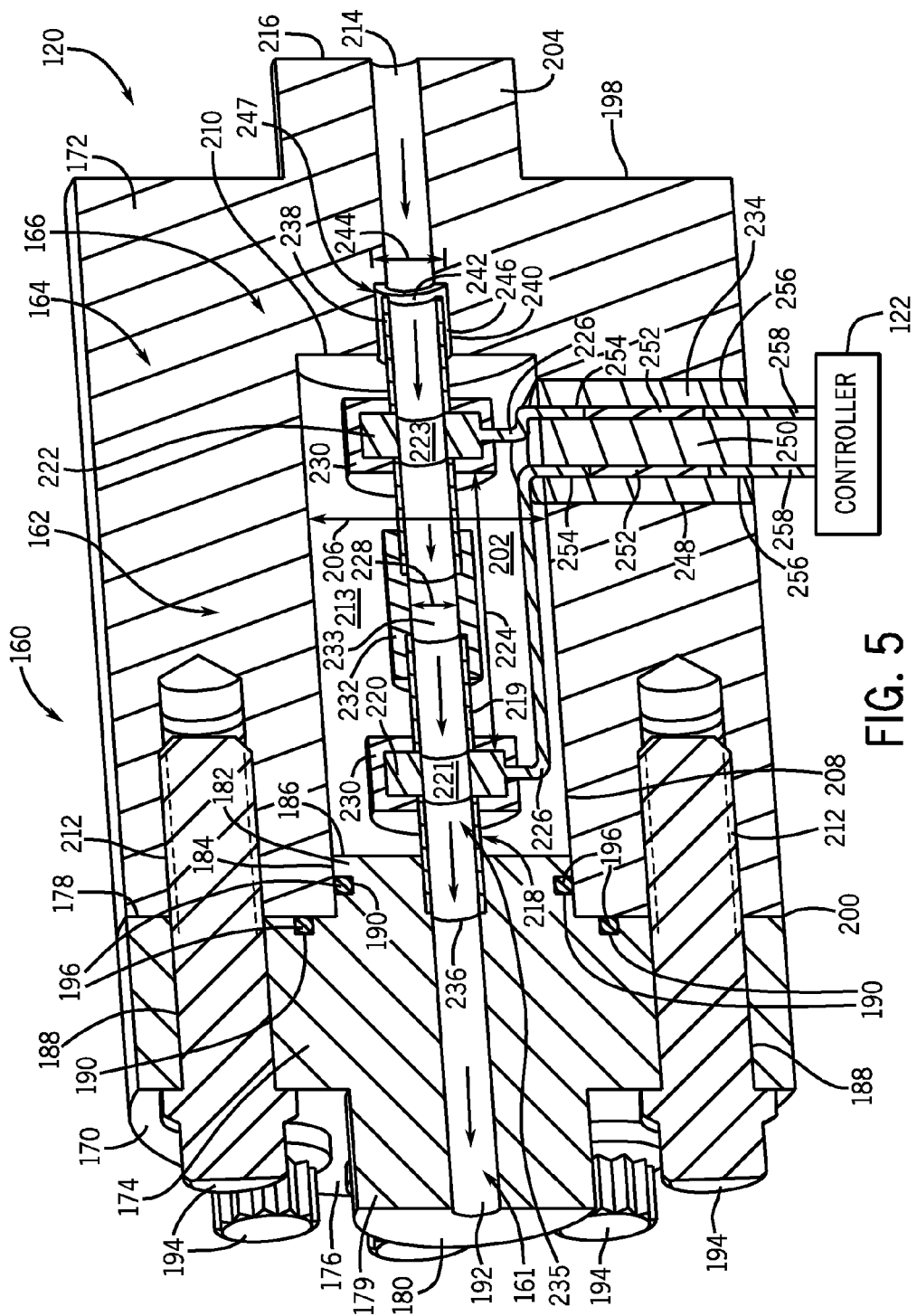
FIG. 5 is a cross-sectional perspective view of an embodiment of a low flow ultrasonic flow meter.

FIG. 5 is a cross-sectional perspective view of an embodiment of a low flow ultrasonic flow meter 120. The flow meter 120 defines a housing 160, ultrasonic meter system 162, acoustic isolator system 164, and a pressure balance system 166. As discussed in detail below, the housing 160 defines a chamber 213 surrounding a conduit 218, wherein the chamber 213 includes the ultrasonic meter system 162, the acoustic isolator system 164, and the pressure balancing system 166. In the illustrated embodiment, the housing 160 includes a lid 170 that connects to a body portion 172. The lid 170 includes a midsection 174 with a front face 176 and a rear face 178. A circular protrusion 179 extends from the front face 176 to an end face 180. The lid's 170 rear face 178 similarly includes a circular protrusion 182, which has a side face 184 an end face 186.

The lid 170 may include multiple apertures. For example, the lid 170 includes multiple bolt apertures 188, gasket apertures 190, and a fluid passage 192. The bolt apertures 188 receive bolts 194, while the gasket apertures receive gaskets 196 (e.g., annular gaskets or seals). In the present embodiments, the gasket apertures 190 and gaskets 196 are located on the rear face 178 of the lid 170, and the side face 184 of the circular protrusion 182. These gaskets 196 form a fluid tight seal between the lid 170 and the body 172. The fluid passage 192 extends between the face 180 of the circular protrusion 179 and the face 186 of the circular protrusion 182. This allows fluid to flow through the lid 170, e.g., fluid flow measured by the flow meter 120.

The body 172 defines a front face 198, a rear face 200, a flow meter aperture 202, and a circular protrusion 204 extending from the front face 198. The flow meter aperture 202 defines a diameter 206, an inner surface 208, and a wall 210. The rear face 200 further defines bolt apertures 212. The lid 170 attaches to the body 172 by inserting the circular protrusion 182 into the flow meter aperture 202. As mentioned above, the flow meter aperture 202 defines a diameter 206, which is equal to or greater than the circular protrusion 182. The protrusion 182 slides into the aperture 202 until the rear face 178 of the lid 170 contacts the rear surface 200 of the body 172. The lid 170 may then be circumferentially rotated about the body 172 until the bolt apertures 188 align with the bolt apertures 212. The bolts 194 extend into the apertures 188, 212 and threadingly secure the lid 170 to the body 172. As explained above, the gaskets 196 are compressed between the two rear faces 178 and 200, and between the inner surface 208 and the surface 184 to create a fluid tight seal between the lid 170 and the body 172. The joining of the lid 170 to the body 172 creates a flow meter chamber/static fluid chamber 213 that houses the ultrasonic meter system 162, acoustic isolation system 164, and pressure balance system 166.

The ultrasonic flow meter 120 includes a through passage 161 defined by passage 192 in the lid 170, a passage 214 in the body 172, and a conduit 218 extending through the chamber 213 between passages 192 and 214. The ultrasonic meter system 162 measures parameters, e.g., a flow rate, along the passage 161. The passage 214 extends between the face 216 of the protrusion 204 and wall 210. Accordingly, fluid may enter the flow meter 120 through the passage 214, flow through the body 172 into the chamber 213, flow through conduit 218 to the passage 192, and then exit through the passage 192 of the lid 170.

As the fluid passes through the flow meter 120, the ultrasonic meter system 162 measures its flow rate. The ultrasonic meter system 162 includes conduit 218, ultrasonic transducers 220 and 222, and controller 122. As illustrated, the transducers 220 and 222 are annular in shape. In other embodiments, the transducers 220 and 222 may vary in shape, e.g., flat, square, oval, etc. The transducers 220 and 222 measure the fluid entering the flow meter 120 and traveling through the conduit 218. As illustrated, the ultrasonic transducers 220 and 222 are mounted around the conduit 218 at an axial offset distance 224 relative to one another. The ultrasonic transducers 220 and 222 measure flow speeds by rapidly sending and receiving ultrasonic waves that travel through the fluid in the conduit 218. For example, the upstream transducer 222 may send ultrasonic waves through the fluid traveling in conduit 218 to the downstream transducer 220. The controller 122 collects the transmission times by the upstream transducer 222 and the reception times by the downstream transducer 220 through wires 226. The controller 122 then calculates ultrasonic wave speed in the fluid using the distance 224 and the time between transmission and reception. The ultrasonic wave speed is then compared to the known speed of ultrasonic waves in the same fluid over the same distance, while the fluid is motionless. The wave speed differences determine how fast the fluid is moving in the conduit 218, i.e., the faster the fluid speed in conduit 218 the less time it takes the ultrasonic waves to travel from the upstream transducer 222 to the downstream transducer 220. Similarly, the faster the fluid speed the longer it will take the ultrasonic waves to travel from the transmitting downstream transducer 220 to the receiving upstream transducer 222. Once fluid speed is known, the controller 122 may calculate flow rate by multiplying the fluid speed by $\pi d^2/4$ (i.e., conduit area), wherein "d" equals the diameter 228 of conduit 218. With this information, the flow regulator 32 may increase, decrease, or maintain the chemical fluid flow rate, e.g., through operation of the valve 126 (as illustrated in FIG. 4). In some embodiments, both transducers 220 and 222 may transmit and receive ultrasonic waves, which the controller 122 may use to determine fluid speed in the pipe. The comparison of the two speeds may advantageously provide increased accuracy of the fluid speed calculation.

As mentioned above, the flow meter 120 may include an acoustic isolation system 164. The acoustic isolation system 164 is configured to block acoustic noise and communications outside of the fluid in the conduit 218, thereby ensuring that the transducers 220 and 222 communicate only through the fluid in the conduit 218 without interference. This acoustic isolation enables more accurate sensing of the fluid flow rate inside the conduit 218. For example, the acoustic isolation system 164 may enable accurate measurement of flow rates as low as 0.03 liters/hour (e.g., less than 0.05, 1, 2, 3, 4, 5, 10, 15, or 20 liters/hour), and as high as 120 liters/hour. In the present embodiment, the acoustic isolation system 164 may use polyether ether ketone (PEEK) to block and/or absorb acoustic noise, interference, and ultrasonic waves created by the transducers 220 and 222 outside of the fluid in the conduit 218. Other embodiments may use a different material to block and/or absorb the ultrasonic wave energy, acoustic noise, or interference. For example, the acoustic isolation system 164 may encapsulate the transducers 220 and 222 with isolative structures 230 (e.g., acoustic damping structures). As illustrated, the isolative structures 230 are ring shaped, but may form other shapes, e.g., square, irregular, oval, rectangular etc. Furthermore, these isolative structures 230 may be made of an acoustic damping material, such as PEEK, an elastomer, a polymer, a foam, or a combination thereof. These PEEK rings 230 absorb ultrasonic waves created by their respective transducer 220 or 222, and waves created by the opposing transducer 220 or 222 outside of the fluid in the conduit 218. For example, the PEEK rings 230 may absorb ultrasonic wave energy transmitted through fluid in chamber 213, and through the wall 219 of conduit 218. For example, the PEEK ring 230 covering transducer 220 absorbs waves produced by transducer 220 and by transducer 222 outside of the conduit 218, while enabling the transducer 220 to transmit and receive ultrasonic wave energy at an interface 221 with the conduit 218. Similarly, the ring 230 covering transducer 222 absorbs waves produced by transducer 222 and by transducer 220 outside of the conduit 218, while enabling the transducer to transmit and receive ultrasonic wave energy at an interface 223 with the conduit 218.

In addition to PEEK rings 230, the acoustic isolator system 164 may include a third acoustic isolative structure 232 (e.g., acoustic damping structure) for absorbing acoustic noise, interference, and ultrasonic waves created by the transducers 220 and 222 outside of the conduit 218. For example, the third acoustic isolative structure 232 may absorb acoustic noise, interference, and ultrasonic waves traveling through the wall 219 of the conduit 218. The ultrasonic waves traveling through the conduit wall 219 may travel at a different speed than the ultrasonic waves traveling through the fluid, and thus the acoustic isolative structure 232 absorbs this energy to improve measurement accuracy. Accordingly, the acoustic isolative structure 232 is mounted axially between the transducers 220 and 222. As illustrated, the acoustic isolative structure 232 encircles and extends along the conduit 218, while also including a conduit interruption or annular blockade 233 axially between portions of the conduit 218. In the illustrated embodiment, the system 164 includes a single third ring 232, while other embodiments may include other shapes of the isolative structure 232, e.g., square, oval, rectangular, irregular, etc. Furthermore, the system 164 may include 1, 2, 3, 4, 5, 6, 7, 8, 9, 10, or more isolative structures 232 between the transducers 220 and 222. Furthermore, each of these structures 232 may vary in thickness and/or type of acoustic material.

Finally, the flow meter 120 may include a pressure balance system 166 that protects the transducers 220 and 222 in high pressures environments. In certain embodiments, the pressures may range between approximately 0 to 50,000 psi, while the flow rates may range between approximately 0.01 to 1000 liters/hour. For example, the flow meter may be configured to measure low flow rates less than approximately 0.01, 0.02, 0.03, 0.04, 0.05, 0.1, 0.2, 0.3, 0.4, 0.5, 0.6, 0.7, 0.8, 0.9, 1, 2, 3, 4, 5, 10, 15, 20, or 25 liters/hour, while operating under pressures up to or greater than 5,000 psi, 10,000 psi, 15,000 psi, 20,000 psi, 25,000 psi, 30,000 psi, 40,000 psi, or 50,000 psi. The pressure balance system 166 includes the chamber 213, conduit 218, and electrical connector plug 234. As illustrated, the conduit 218 includes the wall 219 that surrounds a passage 235 that extends through the chamber 213 from a first end 236, to a second end 238. The first end 236 is coupled to the passage 192 in the lid 170. The second end 239 extends into a counterbore 240 of the wall 210 of the body portion 172. The first end 236 is sealed relative to the passage 192, while the second end 238 is not sealed to the passage 214. Instead, an axial gap 242 exists between the second end 238 and the passage 214. In addition, the counterbore 240 defines a diameter 244 greater than the conduit diameter 228, thereby creating an annular gap 246. The combination of the gaps 242 and 246 creates a fluid connection 247 between the chamber 213, the conduit 218, and the passage 214. This fluid connection 247 between the fluid in the conduit 218 and the chamber 213 allows for an equalization of pressure.

Without pressure equalization, the conduit may compress or expand to the point that transducers 220 and 222 break or lose their connection with the conduit 218. For example, if the pressure in the conduit 218 exceeds the pressure inside the chamber 213 the conduit wall 219 may expand diametrically. Similarly, if the pressure in the chamber 213 exceeds the pressure in the conduit 218, then the wall 219 may compress diametrically. The compression and expansion of the conduit wall 219 may cause the transducers 220, 222 to break or separate from the conduit 218, preventing proper transmission and reception of ultrasonic waves traveling through the fluid in the conduit 218. Thus, the fluid connection 247 enables the fluid to pressure balance between the chamber 213 and the conduit 218 to increase an operational range of the flow meter 120 to higher pressures, e.g., greater than 10,000 psi, 15,000 psi, 20,000 psi, 25,000 psi, 30,000 psi, 40,000 psi, or 50,000 psi.

The electrical connection plug 234 maintains communication between the ultrasonic meter system 162 and the controller 122. More specifically, the electrical connection plug 234 permits electrical communication between the transducers 220 and 222, while maintaining pressure and a fluid tight seal. For example, the electrical connection plug 234 may fit within and adhere to a passage 248 within the body 172. For example, the plug 234 may be threaded, welded, press fitted in the passage 248. The plug 234 may retain fluid within the chamber 213 without leakage at pressures of greater than 10,000 psi, 15,000 psi, 20,000 psi, 25,000 psi, 30,000 psi, 40,000 psi, or 50,000 psi.

The electrical connection plug 234 includes a body portion 250 (e.g., an electrically insulative body portion) and electrically conductive portions 252 (e.g., wires) disposed in apertures 254 and 256. These electrically conductive portions 252 couple to wires 226 from the transducers 220 and 222 and wires 258 from the controller 122. The wires 226 and 258 and the electrically conductive portions 252 enable electrical signals to pass from the transducers 220 and 222 within the flow meter 120 to the exterior controller 122, while the body portion 250 maintains a seal of the chamber 213. Accordingly, the three systems: ultrasonic meter system 162, acoustic isolator system 164, and pressure balance system 166 permit accurate low flow rate measurement in a high-pressure environment.

Figure 6:
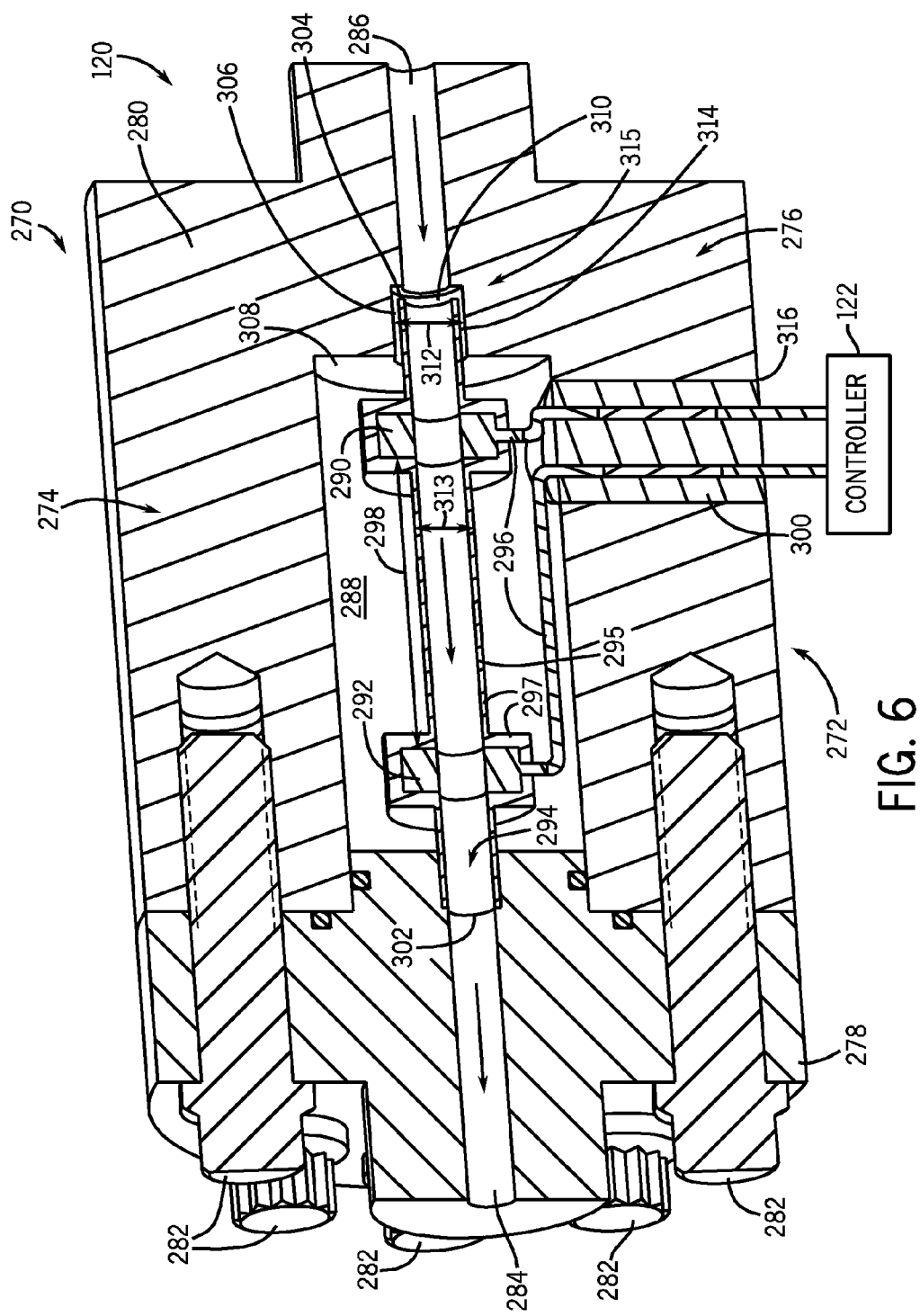
FIG. 6 is a cross-sectional perspective view of an embodiment of a low flow ultrasonic flow meter.

FIG. 6 is a cross-sectional perspective view of an embodiment of a low flow ultrasonic flow meter 120. Similar to the flow meter 120 of FIG. 5, the flow meter 120 in FIG. 6 includes a housing 270, ultrasonic meter system 272, acoustic isolator system 274, and a pressure balance system 276. In the illustrated embodiment, the housing 270 includes a lid 278 that connects to a body portion 280. The lid 278 connects to the body 280 via bolts 282. As illustrated, the lid 278 and the body portion 282 include a passage that allows fluid to pass through the flow meter 120. Specifically, the lid 278 includes an exit passage 284, while the body 280 includes an entrance passage 286 or vice versa. The passages 284 and 286 connect to a chamber 288 within the housing 270.

The ultrasonic meter system 272 is located within the chamber 288, and as discussed above measures the flow rate of fluid through the flow meter 120. The ultrasonic flow meter system 272 includes an upstream transducer 290 and a downstream transducer 292 (or vice versa) that attach to a conduit wall 295 of a conduit 294. The ultrasonic transducers 290 and 292 may send or receive ultrasonic waves to the opposite transducer through the fluid traveling in the conduit 294. The controller 122 receives the transmission and reception times of the ultrasonic waves from the transducers 290 and 292 through electrical connections 296 and then determines their speed using an offset distance 298 between the transducers 290 and 292. As discussed above, the faster a fluid is traveling in the conduit 294, the faster a wave will travel from the upstream transducer 290 to the downstream transducer 292. Likewise, a fast moving fluid will slow a wave traveling against the current from the downstream transducer 292 to the upstream transducer 290. With this information, the controller 122 is able to determine the flow rate of the fluid by comparing the speed of the wave in the flow meter to a known speed of the wave in a motionless fluid.

As mentioned above, the flow meter 120 includes an acoustic isolation system 274. The acoustic isolation system 274 is configured to block acoustic noise and communications outside of the fluid in the conduit 294, thereby ensuring that the transducers 290 and 292 only communicate with each other through the fluid in the conduit 294. This acoustic isolation enables more accurate sensing of the fluid flow rate inside the conduit 294. For example, the acoustic isolation system 274 may advantageously enable accurate measurement of flow rates as low as 0.03 liters/hour (e.g., less than 0.05, 1, 2, 3, 4, 5, 10, 15, or 20 liters/hour), and as high as 120 liters/hour. In the present embodiment, the acoustic isolation system 274 covers the conduit 294; and the transducers 290 and 292 with an acoustic damping material, e.g., a PEEK shell 297. The PEEK shell 297 may block and/or dampen acoustic noise, interference or ultrasonic waves in the chamber 288, thereby substantially reducing interference with the transducers 290 and 292. In other words, the PEEK shell 297 may block or dampen all acoustic waves other then the desired transmission of ultrasonic waves through the fluid in the conduit 294 between the transducers 290 and 292. Furthermore, the PEEK of the shell 297 may also serve as a protective barrier or chemical resistant coating, which may protect the transducers 290 and 292 from corrosion by chemicals in the chamber 288. Thus, the PEEK shell 297 may simultaneously dampen acoustics and chemically protect the transducers 290 and 292. The PEEK shell 297 may also dampen or absorb ultrasonic energy that may be traveling in the conduit wall 295 (i.e., waves travel at a different speed in the conduit wall 295 relative to waves traveling through the fluid in the conduit 294). Thus, the PEEK shell 297 surrounding the conduit 294 and transducers 290 and 292 enables the acoustic isolation system 274 to protect the conduit 294, while absorbing waves not traveling through the fluid in conduit 294.

The flow meter 120 also includes the pressure balance system 276. The pressure balance system 276 includes the chamber 288, conduit 294, and electrical connector plug 300. The pressure balance system 276 allows the ultrasonic meter system 274 to operate in pressure ranges between approximately 0 to 50,000 psi, while the flow rates may range between approximately 0.01 to 1000 liters/hour. For example, the flow meter may be configured to measure low flow rates less than approximately 0.01, 0.02, 0.03, 0.04, 0.05, 0.1, 0.2, 0.3, 0.4, 0.5, 0.6, 0.7, 0.8, 0.9, 1, 2, 3, 4, 5, 10, 15, 20, or 25 liters/hour, while operating under pressures up to or greater than 5,000 psi, 10,000 psi, 15,000 psi, 20,000 psi, 25,000 psi, 30,000 psi, 40,000 psi, or 50,000 psi.

As illustrated, the conduit 294 extends through the chamber 288 from a first end 302, which connects to the passage 284, to a second end 304. The second end 304 sits in a counterbore 306 formed in a wall 308 of the chamber 288. Unlike the first end 302, which connects to passage 284, the second end 304 does not connect to the passage 286. Instead, a gap 310 exists between the second end 304 and the passage 286. In addition, the counterbore 306 defines a diameter 312 that is greater than a diameter 313 of the PEEK covered conduit 294. This distance creates a second gap 314. The combination of the first and second gaps 310, 314 creates a fluid connection 315 between the chamber 288, the conduit 294, and the passage 286. This fluid connection 315 allows for an equalization of pressure between the fluid in the conduit 294 and the chamber 288. The pressure equalization limits or prevents compression and expansion of the conduit 294 that may break the transducers 290 and 292 or cause them to lose their connection to the conduit 294. Finally, as discussed above, the pressure balance system 276 includes the electrical connection plug 300. The electrical connection plug 300 permits electrical communication between the transducers 290 and 292, while maintaining a pressure and fluid tight seal. As illustrated, the electrical connection plug 300 may fit within and adhere to a passage 316 within the body 280. In particular, the plug 300 permits electrical communication between the transducers 290 and 292 with the controller 122, while withstanding pressures up to or greater than approximately 5,000 psi, 10,000 psi, 15,000 psi, 20,000 psi, 25,000 psi, 30,000 psi, 40,000 psi, or 50,000 psi.

Figure 7:
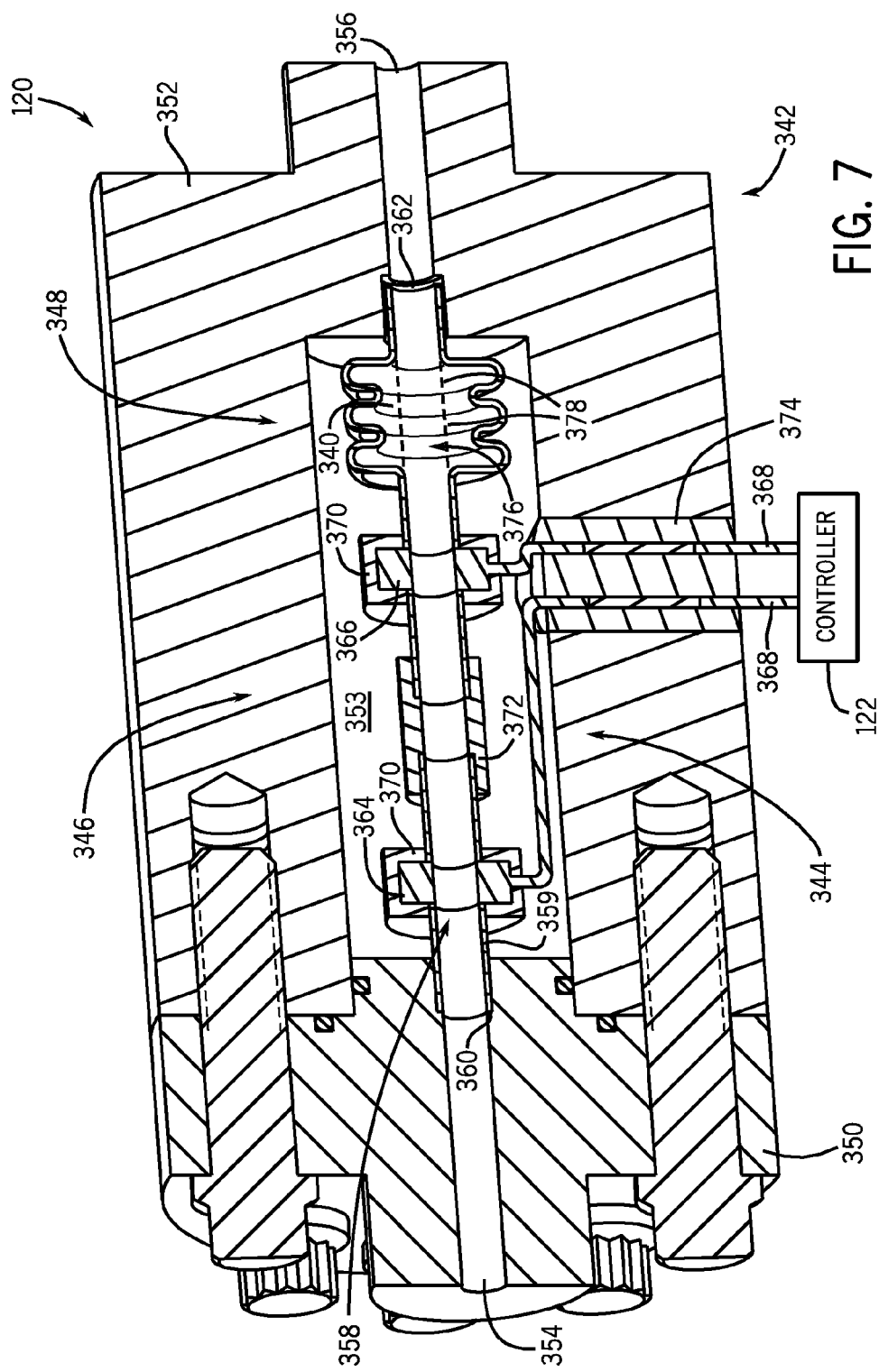
FIG. 7 is a cross-sectional perspective view of an embodiment of a low flow ultrasonic flow meter with a pressure adjusting mechanism.

FIG. 7 is a cross-sectional side view of an embodiment of a low flow ultrasonic flow meter 120 with pressure equalizing mechanism 340. For example, the pressure equalizing mechanism 340 may include a bellows, such as an expandable and contractible bellows. By further example, the pressure equalizing mechanism 340 may include a bellows, a balloon, a diaphragm, a piston-cylinder assembly, gel slugs in biros, or any combination thereof. For example, the bellows, balloon, or diaphragm may be made of an expandable/compressible material, such as an elastomer. Similar to the flow meter 120 of FIG. 5, the flow meter 120 in FIG. 7 includes a housing 342, ultrasonic meter system 344, acoustic isolator system 346, and a pressure balance system 348. In the illustrated embodiment, the housing 342 includes a lid 350 that connects to a body portion 352. Together, the lid 350 and body portion 352 define a chamber 353. As illustrated, the lid 350 and the body portion 352 each define a passage that allows fluid to pass through the flow meter 120. Specifically, the lid 350 defines an exit passage 354, while the body 352 defines an entrance passage 356 or vice versa. The passages 354 and 356 connect to a conduit 358 at respective first and second ends 360 and 362 of a conduit wall 359.

As illustrated, the ultrasonic meter system 344 includes transducers 364 and 366, electrical lines 368, and controller 122. The ultrasonic transducers 364 and 366 may send or receive ultrasonic waves to the opposite transducer through the fluid traveling in the conduit 358. The controller 122 receives the transmission and reception times of the ultrasonic waves from the transducers 364 and 366 through electrical lines 368, which it then uses to calculate the fluid speed in the conduit 358. As discussed above, the faster a fluid is traveling in the conduit 358 the faster a wave will travel from the upstream transducer 366 to the downstream transducer 364. Likewise, a fast moving fluid will slow a wave traveling against the current from the downstream transducer 364 to the upstream transducer 366. With this information, the controller 122 is able to determine the flow rate of the fluid by comparing the speed of the wave in the flow meter to a known speed of the wave in a motionless fluid.

As illustrated, the flow meter 120 includes the acoustic isolation system 346. The acoustic isolation system 346 uses PEEK rings 370 to prevent the transducers 364 and 366 from communicating with each other except through the fluid traveling in conduit 358. For example, the acoustic isolation system 346 may advantageously allow for accurate measurement of flow rates as low as 0.03 liters/hour (e.g., 0.05, 1, 2, 3, 4, 5, 10, 15, or 20 liters/hour), and as high as 120 liters/hour. In the present embodiment, the acoustic isolation system 346 includes a third PEEK ring 372 for absorbing ultrasonic waves created by the transducer 364 and 366. The ring 372 is disposed axially between the transducers 364 and 366, such that it absorbs ultrasonic wave energy traveling through the conduit wall 359. While the present embodiments illustrate a single third ring 372, in other embodiments there may be more rings in-between the transducers 364 and 366. For example, there may be 1, 2, 3, 4, 5, 6, 7, 8, 9, or 10 rings in-between the transducers 364 and 366. Furthermore, each of these rings may vary in thickness and or type of absorbing material with respect to the other rings. In the present embodiment, the pressure equalizing mechanism 340 (e.g., bellows) may permit a second fluid to occupy the chamber 353 surrounding the conduit 358 such that the second fluid is isolated from the first fluid flowing through the conduit 350. The second fluid may be specifically selected based on acoustic damping properties, e.g., the second fluid may be a protective liquid that will not corrode the housing 342, the PEEK rings 370 and 372, or otherwise negatively affect the system. For example, the second fluid may include oil. In some embodiments, the second fluid may advantageously include fine particles that promote acoustic damping (e.g., sand, beads, foam, etc.).

The flow meter 120 may also include the pressure balance system 348. The pressure balance system 348 includes the chamber 353, conduit 358, pressure equalizing mechanism 340 (e.g., bellows), and electrical connector plug 374. The pressure balance system 348 allows the ultrasonic meter system 344 to operate in pressure ranges between approximately 0 to 50,000 psi, while the flow rates may range between approximately 0.01 to 1000 liters/hour. For example, the flow meter may be configured to measure low flow rates less than approximately 0.01, 0.02, 0.03, 0.04, 0.05, 0.1, 0.2, 0.3, 0.4, 0.5, 0.6, 0.7, 0.8, 0.9, 1, 2, 3, 4, 5, 10, 15, 20, or 25 liters/hour, while operating under pressures up to or greater than 5,000 psi, 10,000 psi, 15,000 psi, 20,000 psi, 25,000 psi, 30,000 psi, 40,000 psi, or 50,000 psi.

As illustrated, the pressure equalizing mechanism 340 (e.g., bellows) replaces or extends around a section 376 of the conduit 358. The pressure equalizing mechanism 340 (e.g., bellows) may be made out of metal, rubber, neoprene, vinyl, silicone, or other material that expands and contracts in response to changes in pressure. The expansion and contraction of the pressure equalizing mechanism 340 (e.g., bellows) advantageously permits pressure equalization, while allowing a second fluid to occupy the chamber 353. For example, the conduit 358 may include perforations or passages 378 on the section 376 to enable fluid traveling through the conduit 358 to enter the pressure equalizing mechanism 340 (e.g., bellows). Thus, during an increase in pressure in the conduit 358, the fluid passes through the passages 378 and into the pressure equalizing mechanism 340 (e.g., bellows), causing expansion of the pressure equalizing mechanism 340 (e.g., bellows) to pressure equalize with the chamber 353. Likewise, during a decrease in pressure in the conduit 358, the pressure equalizing mechanism 340 (e.g., bellows) contracts and forces fluid through the passages 378 in the section 376 and into the conduit 358, thereby enabling pressure equalization as the pressure equalizing mechanism 340 (e.g., bellows) expands and contracts in response to pressure changes, accordingly, the conduit 358 does not experience significant stresses (i.e., the conduit 358 does not expand or compress). As explained above, the expansion and contraction of the conduit 358 may break or loosen the connection of the transducers 366 and 368, which may prevent or limit accurate measurement. Finally, the pressure balance system 348 includes an electrical connection plug 374. The electrical connection plug 374 permits electrical communication between the transducers 364 and 366 and the controller 122, while maintaining a fluid tight seal under significant pressure.

Figure 8:
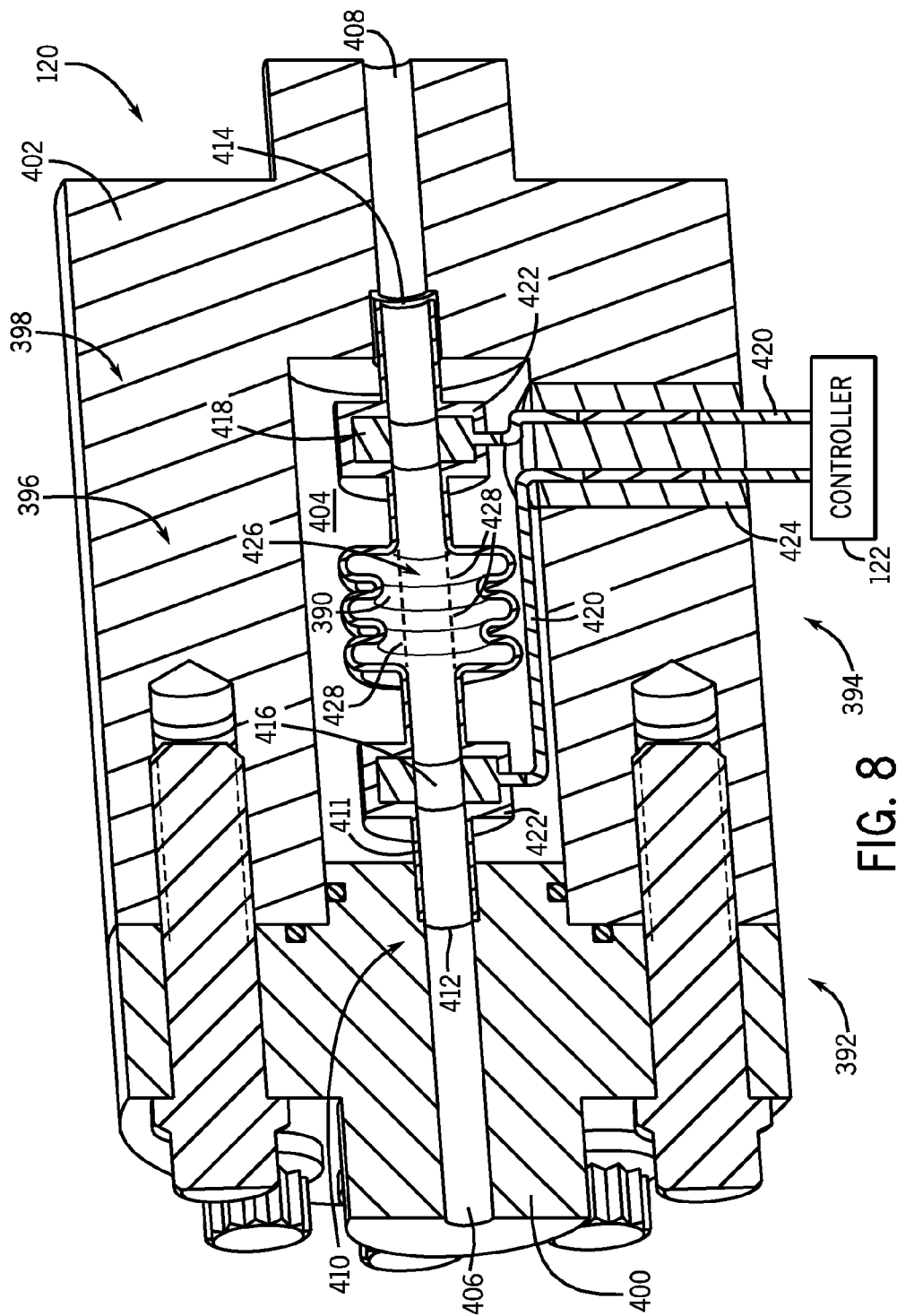
FIG. 8 is a cross-sectional perspective view of an embodiment of a low flow ultrasonic flow meter with a pressure adjusting mechanism.

FIG. 8 is a cross-sectional side view of an embodiment of a low flow ultrasonic flow meter 120 with a PEEK pressure equalizing mechanism 390 for pressure equalization, acoustic damping, and corrosion protection. In certain embodiments, the pressure equalizing mechanism 390 may include a bellows, a balloon, a diaphragm, a piston-cylinder assembly, gel slugs in biros, or any combination thereof. Similar to the flow meter 120 of FIG. 7, the flow meter 120 in FIG. 8 includes a housing 392, ultrasonic meter system 394, acoustic isolator system 396, and a pressure balance system 398. In the illustrated embodiment, the housing 392 includes a lid 400 that connects to a body portion 402. Together, the lid 400 and body portion 402 define a chamber 404. As illustrated, the lid 400 and the body portion 402 each define a passage that allows fluid to pass through the flow meter 120. Specifically, the lid 400 defines an exit passage 406, while the body 402 defines an entrance passage 408 or vice versa. The passages 406 and 408 connect with a conduit 410 at respective first and second ends 412 and 414 of a conduit wall 411.

As illustrated, the ultrasonic meter system 394 includes transducers 416 and 418, electrical lines 420, and controller 122. The ultrasonic transducers 416 and 418 may send or receive ultrasonic waves to the opposite transducer through the fluid traveling in the conduit 410. As explained above, the controller 122 uses the transmission and reception of the ultrasonic waves between the transducers 416 and 418 to calculate the flow rate of the fluid in the conduit 410.

Furthermore, the flow meter 120 includes the acoustic isolation system 396. The acoustic isolation system 396 uses PEEK rings 422 and a PEEK pressure equalizing mechanism 390 (e.g., bellows) to prevent the transducers 416 and 418 from communicating with each other except through the fluid traveling in conduit 410. For example, PEEK rings 422 encapsulate the transducers 416 and 422 preventing them from transmitting ultrasonic waves through the fluid in the chamber 404. As illustrated, the PEEK pressure equalizing mechanism 390 (e.g., bellows) may also be included axially between the transducers 416 and 422. The PEEK pressure equalizing mechanism 390 (e.g., bellows) effectively absorbs ultrasonic energy traveling through the conduit wall 411, thus, only ultrasonic waves traveling in the fluid reach the transducers 416 and 422. In some embodiments, the PEEK pressure equalizing mechanism 390 (e.g., bellows) may permit a second fluid to occupy the chamber 404 surrounding the conduit 410. The second fluid may be an oil, or other fluid that will not corrode the housing 392, the PEEK rings/bellows 422/390, or otherwise negatively affect the system. The second fluid may advantageously include fine particles that promote acoustic damping (e.g., sand, beads, foam, etc.).

The flow meter 120 may also include the pressure balance system 398. The pressure balance system 398 includes the pressure equalizing mechanism 390 (e.g., bellows), chamber 404, conduit 410, and electrical connector plug 424. The pressure balance system 398 allows the ultrasonic meter system 394 to operate in pressure ranges between approximately 0 to 50,000 psi, while the flow rates may range between approximately 0.01 to 1000 liters/hour. For example, the flow meter may be configured to measure low flow rates less than approximately 0.01, 0.02, 0.03, 0.04, 0.05, 0.1, 0.2, 0.3, 0.4, 0.5, 0.6, 0.7, 0.8, 0.9, 1, 2, 3, 4, 5, 10, 15, 20, or 25 liters/hour, while operating under pressures up to or greater than 5,000 psi, 10,000 psi, 15,000 psi, 20,000 psi, 25,000 psi, 30,000 psi, 40,000 psi, or 50,000 psi.

As illustrated, the conduit 410 may include the PEEK pressure equalizing mechanism 390 (e.g., bellows) replacing or extending around a section 426 of the conduit 410. The pressure equalizing mechanism 390 (e.g., bellows) advantageously permits pressure equalization by expanding when the fluid traveling in conduit 410 increases in pressure, and contracting when the pressure drops. For example, the conduit 410 may have one or more passages 428 formed in the section 426 within the pressure equalizing mechanism 390 (e.g., bellows). As the chemical fluid flowing through the conduit 410 experiences an increase in pressure, the fluid flows out of the section 426 through passages 428 and into the bellows section 390, causing it to expand. Similarly, if the chemical fluid reduces in pressure in the conduit 410, then the fluid leaves the pressure equalizing mechanism 390 (e.g., bellows) and enters the conduit 410, thereby enabling pressure equalization. The expansion and contraction of the pressure equalizing mechanism 390 (e.g., bellows) reduces or eliminates pressure differentials that could cause expansion or contraction of the conduit 410. As explained above, the expansion and contraction of the conduit 410 may break or loosen the connection of the transducers 416 and 418, which may prevent or limit accurate measurement. Finally, as discussed above, the pressure balance system 398 includes the electrical connection plug 424. The electrical connection plug 424 permits electrical communication between the transducers 416 and 418, and the controller 122, while maintaining a fluid tight seal under pressure.

Figure 9:
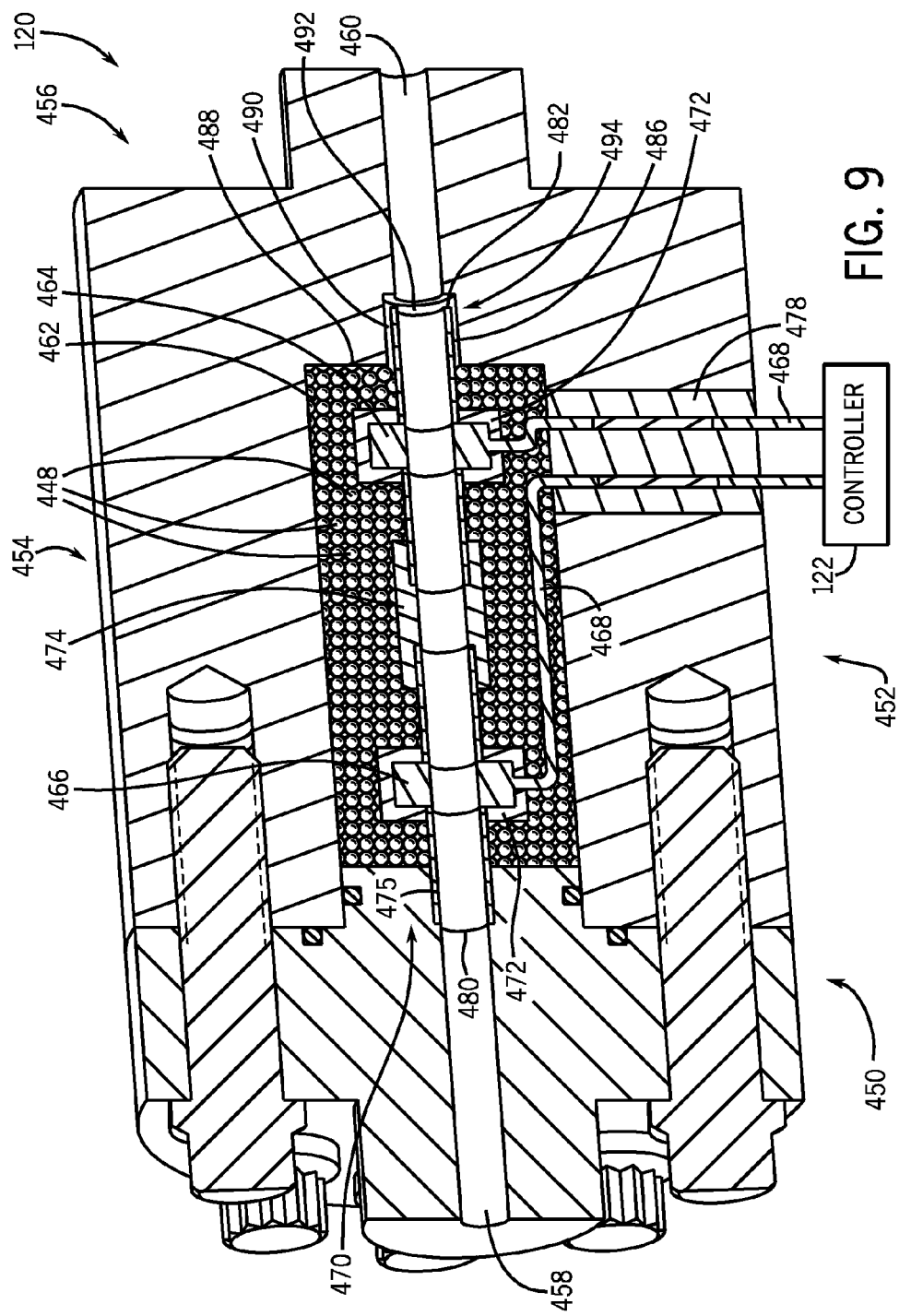
FIG. 9 is a cross-sectional perspective view of an embodiment of a low flow ultrasonic flow meter with acoustic signal damping particles.

FIG. 9 is a cross-sectional side view of an embodiment of a low flow ultrasonic flow meter 120 with particles 448 configured to dampen acoustical noise. Similar to the flow meter 120 of FIG. 5, the flow meter 120 in FIG. 9 includes a housing 450, ultrasonic meter system 452, acoustic isolation system 454, and a pressure balance system 456. In the illustrated embodiment, the housing 450 defines passages that allow fluid to pass through the flow meter 120, specifically, an exit passage 458 and an entrance passage 460 or vice versa. In addition, the housing 450 defines a chamber 462 that houses the ultrasonic meter system 452, the acoustic isolation system 454, and the pressure balance system 456.

As illustrated, the ultrasonic meter system 452 includes transducers 464 and 466, electrical lines 468, and controller 122. The ultrasonic transducers 464 and 466 may send or receive ultrasonic waves to the opposite transducer through the fluid traveling in the conduit 470. As explained above, the controller 122 uses the transmission and reception of the ultrasonic waves between the transducers 464 and 466 to calculate the flow rate of the fluid in the conduit 470.

As illustrated, the flow meter 120 includes the acoustic isolation system 454. The acoustic isolation system 454 uses PEEK rings 472 to prevent the transducers 464 and 466 from communicating with each other except through the fluid traveling in conduit 470. For example, the acoustic isolation system 454 may allow for accurate measurement of flow rates as low as 0.03 liters/hour (e.g., less than 0.05, 1, 2, 3, 4, 5, 10, 15, or 20 liters/hour), and as high as 120 liters/hour. In the present embodiment, the acoustic isolation system 454 includes a third PEEK ring 474 for absorbing ultrasonic wave energy traveling through conduit wall 475. While the present embodiments illustrate a single third ring 474, in other embodiments there may be more rings of similar or varying sizes in-between the transducers 464 and 466. In addition to the rings 472 and 474, the acoustic isolation system 454 may include particles 448 within the chamber 462. The particles 448 may absorb acoustic noise traveling through the fluid in the chamber 462, while simultaneously limiting fluid motion in chamber 462, i.e., limiting fluid motion prevents the creation of acoustical noise. The particles may also deflect the acoustical noise, i.e., preventing the waves from traveling in a straight path, which may help block acoustics. The particles 448 may be made out of PEEK, rubber, neoprene, vinyl, silicone or other substances that may absorb acoustic noise and are capable of enduring a chemical environment. Furthermore, the particles 448 may take on a variety of shapes and sizes, e.g., circular, oval, irregular, etc.

The flow meter 120 may also include the pressure balance system 456. The pressure balance system 456 includes the chamber 462, conduit 470, and electrical connector plug 478. The pressure balance system 456 allows the ultrasonic meter system 452 to operate in pressures between approximately 0 to 50,000 psi, while the flow rates may range between approximately 0.01 to 1000 liters/hour. For example, the flow meter may be configured to measure low flow rates less than approximately 0.01, 0.02, 0.03, 0.04, 0.05, 0.1, 0.2, 0.3, 0.4, 0.5, 0.6, 0.7, 0.8, 0.9, 1, 2, 3, 4, 5, 10, 15, 20, or 25 liters/hour, while operating under pressures up to or greater than 5,000 psi, 10,000 psi, 15,000 psi, 20,000 psi, 25,000 psi, 30,000 psi, 40,000 psi, or 50,000 psi.

As illustrated, the conduit 470 extends through the chamber 462 from a first end 480, which connects to the passage 458, to a second end 482. The second end 482 sits in a counterbore 486 formed in a wall 488 of the chamber 462. Unlike the first end 480, which connects to passage 458, the second end 482 does not connect to the passage 460 or the side surface 490 of the counterbore 486. This produces a gap 492 that allows a fluid connection 494 between the chamber 462, the conduit 470, and the passage 460. The fluid connection 494 allows for an equalization of pressure between the fluid in the conduit 470 and the chamber 462. The pressure equalization limits or prevents compression and expansion of the conduit 470 that may break the transducers 464 and 466 or cause them to lose their connection to the conduit 470. Finally, as discussed above, the pressure balance system 456 includes the electrical connection plug 478. The electrical connection plug 478 permits electrical communication between the transducers 464 and 466 and the controller 122.

Figure 10:
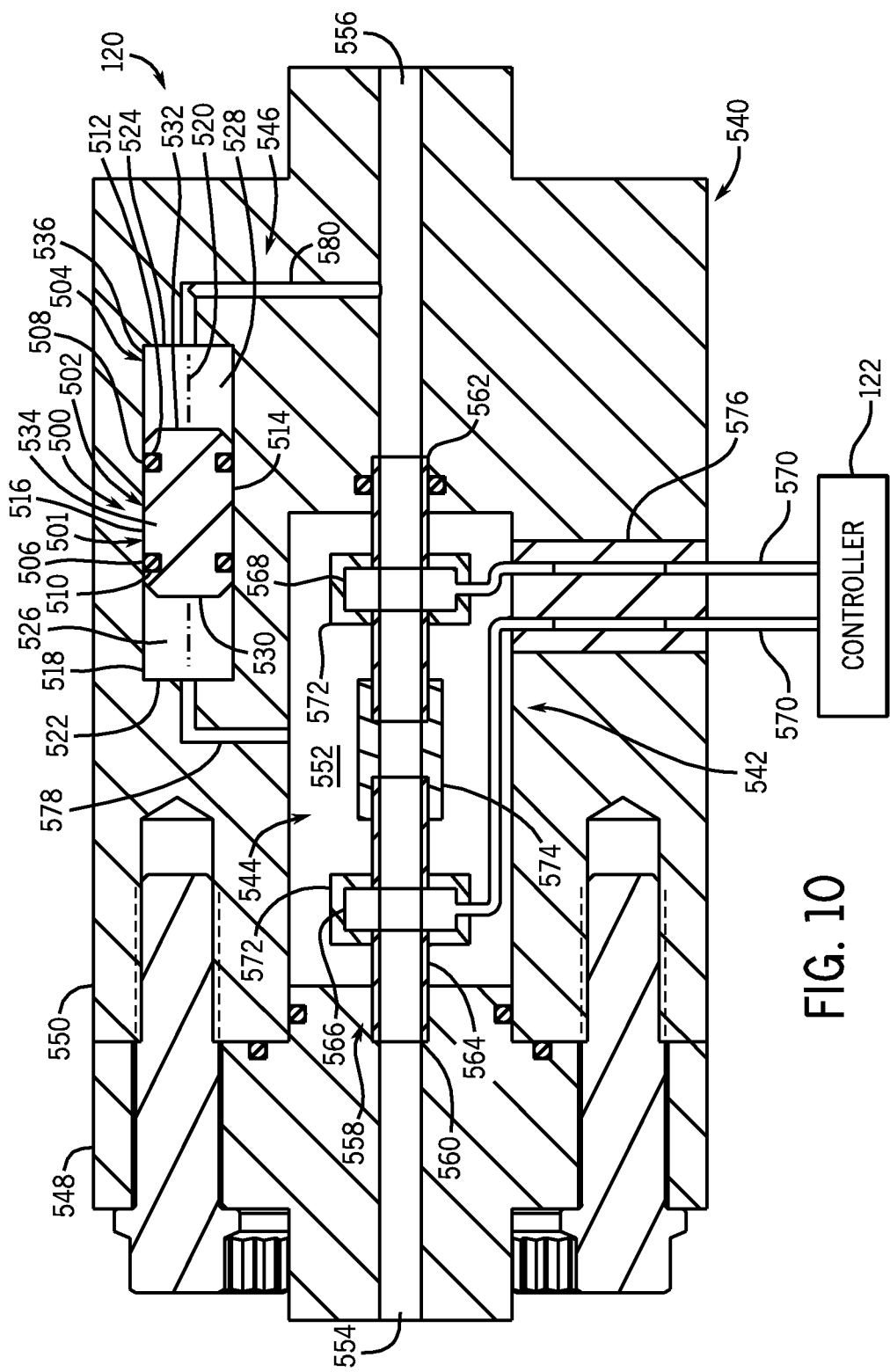
FIG. 10 is a cross-sectional view of an embodiment of a low flow ultrasonic flow meter with a pressure adjusting mechanism.

FIG. 10 is a cross-sectional side view of an embodiment of a low flow ultrasonic flow meter 120 with a pressure equalizing mechanism 500. For example, the pressure equalizing mechanism 500 may include a piston-cylinder assembly 501 having a piston 502 disposed in a cylinder 504. In the illustrated embodiment, the piston 502 includes one or more seals, such as first and second annular seals or rings 506 and 508, which are disposed in annular seal grooves 510 and 512, respectively. The piston 502 may be made of any suitable material, such as metal, plastic, ceramic, cermet, or any combination thereof. For example, the piston 502 may be made of a stainless steel. Furthermore, the seals 506 and 508 may be made from any suitable material, such as metal, plastic, fabric, or any combination thereof. In some embodiments, the piston 502 may exclude the seals 506 and 508 and associated seal grooves 510 and 512. Some embodiments also may employ a coating 514 disposed along an exterior surface 516 of the piston 502 and/or an interior surface 518 of the cylinder 504. The coating 514 may include a corrosion resistant coating, a wear resistant coating, a low friction coating, or any combination thereof. For example, the coating 514 may include a low friction coating, such as polytetrafluoroethylene (PTFE) or Teflon. By further example, the coating 514 may include a wear resistant coating, such as tungsten carbide.

In the illustrated embodiment, the piston 502 moves along an axis 520 of the cylinder 504 between opposite first and second ends 522 and 524 of the cylinder 504 in response to pressure changes between opposite first and second fluid chambers 526 and 528, respectively. In particular, the first fluid chamber 526 is defined between the first end 522 of the cylinder 504 and a first end 530 of the piston 502, while the second fluid chamber 528 is defined between the second end 524 of the cylinder 504 and a second end 532 of the piston 502. As the pressure changes in the first and second fluid chambers 526 and 528, the piston 502 moves along the axis 520 of the cylinder 504 to pressure balance the first and second fluid chambers 526 and 528. In the illustrated embodiment, the piston 502 has a cylindrical shaped body 534, which may be solid or hollow. Similarly, the cylinder 504 has a cylindrical shaped geometry 536 to accommodate the cylindrical shaped body 534 of the piston 502. However, other embodiments of the piston 502 and the cylinder 504 may have other geometrical shapes, such as oval, rectangular, polygonal, and so forth. Furthermore, some embodiments of the pressure equalizing mechanism 500 may include a plurality of pistons 502 disposed in the cylinder 504, or a plurality of piston-cylinder assemblies 501 each having at least one piston 502 disposed in a cylinder 504. In other embodiments, the piston 504 may be replaced with a bellows, diaphragm, or other pressure balancing mechanism in the cylinder 504. As discussed below, the piston-cylinder assembly 501 is configured to provide pressure balancing to increase the operational pressure range of the low flow ultrasonic flow meter 120.

In addition, the low flow ultrasonic flow meter 120 of FIG. 10 includes a housing 540, ultrasonic meter system 542, acoustic isolator system 544, and a pressure balance system 546. In the illustrated embodiment, the housing 540 includes a lid 548 that connects to a body portion 550. Together, the lid 548 and body portion 550 define a chamber 552. As illustrated, the lid 548 and the body portion 550 each define a passage that allows fluid to pass through the flow meter 120. Specifically, the lid 548 defines a first passage 554, while the body 550 defines a second passage 556. In one embodiment, the first passage 554 is an entrance passage while the second passage 556 is an exit passage. In another embodiment, the first passage 554 is an exit passage while the second passage 556 is an entrance passage. The passages 554 and 556 connect to a conduit 558 at respective first and second ends 560 and 562 of a conduit wall 564.

As illustrated, the ultrasonic meter system 542 includes transducers 566 and 568, electrical lines 570, and controller 122. The ultrasonic transducers 566 and 568 may send or receive ultrasonic waves to the opposite transducer through the fluid traveling in the conduit 558. The controller 122 receives the transmission and reception times of the ultrasonic waves from the transducers 566 and 568 through electrical lines 570, which it then uses to calculate the fluid speed in the conduit 558. As discussed above, the faster a fluid is traveling in the conduit 558 the faster a wave will travel from the upstream transducer 568 to the downstream transducer 566, or vice versa. Likewise, a fast moving fluid will slow a wave traveling against the current from the downstream transducer 566 to the upstream transducer 568, or vice versa. With this information, the controller 122 is able to determine the flow rate of the fluid by comparing the speed of the wave in the flow meter to a known speed of the wave in a motionless fluid.

As further illustrated in FIG. 10, the flow meter 120 includes the acoustic isolation system 544. The acoustic isolation system 544 uses acoustic isolation rings 572 to prevent the transducers 566 and 568 from communicating with each other except through the fluid traveling in conduit 558. For example, the acoustic isolation rings 572 may be made of an acoustic isolation material, such as PEEK, and thus the rings 572 may be described as PEEK rings 572. The acoustic isolation system 544 may advantageously allow for accurate measurement of flow rates as low as 0.03 liters/hour (e.g., 0.05, 1, 2, 3, 4, 5, 10, 15, or 20 liters/hour), and as high as 120 liters/hour. In the present embodiment, the acoustic isolation system 544 includes a third acoustic isolation ring 574 (e.g., a PEEK ring) for absorbing ultrasonic waves created by the transducer 566 and 568. The ring 574 is disposed axially between the transducers 566 and 568, such that it absorbs ultrasonic wave energy traveling through the conduit wall 564. While the present embodiments illustrate a single third ring 574, in other embodiments there may be more rings in-between the transducers 566 and 568. For example, there may be 1, 2, 3, 4, 5, 6, 7, 8, 9, or 10 rings in-between the transducers 566 and 568. Furthermore, each of these rings may vary in thickness and or type of absorbing material with respect to the other rings. In the present embodiment, the pressure equalizing mechanism 500 (e.g., piston-cylinder assembly 501) may permit a second fluid to occupy the chamber 552 surrounding the conduit 558 such that the second fluid is isolated from the first fluid flowing through the conduit 548. The second fluid may be specifically selected based on acoustic damping properties, e.g., the second fluid may be a protective liquid that will not corrode the housing 540, the PEEK rings 572 and 574, or otherwise negatively affect the system. For example, the second fluid may include oil. In some embodiments, the second fluid may advantageously include fine particles that promote acoustic damping (e.g., sand, beads, foam, etc.).

The flow meter 120 may also include the pressure balance system 546. The pressure balance system 546 includes the chamber 552, conduit 558, pressure equalizing mechanism 500 (e.g., piston-cylinder assembly 501), and electrical connector plug 576. The pressure balance system 546 allows the ultrasonic meter system 542 to operate in pressure ranges between approximately 0 to 50,000 psi, while the flow rates may range between approximately 0.01 to 1000 liters/hour. For example, the flow meter may be configured to measure low flow rates less than approximately 0.01, 0.02, 0.03, 0.04, 0.05, 0.1, 0.2, 0.3, 0.4, 0.5, 0.6, 0.7, 0.8, 0.9, 1, 2, 3, 4, 5, 10, 15, 20, or 25 liters/hour, while operating under pressures up to or greater than 5,000 psi, 10,000 psi, 15,000 psi, 20,000 psi, 25,000 psi, 30,000 psi, 40,000 psi, or 50,000 psi.

In the illustrated embodiment, the pressure equalizing mechanism 500 (e.g., piston-cylinder assembly 501) is radially offset away from the fluid chamber 552, but connects both to the fluid chamber 552 and the fluid flow path through the flow meter 120. For example, the illustrated pressure equalizing mechanism 500 includes first and second conduits or passages 578 and 580, which couple to the first and second fluid chambers 526 and 528 of the cylinder 504. Thus, the passage 578 communicates fluid between the fluid chambers 526 and 552, such that the chambers 526 and 552 are at substantially the same pressure as one another. Likewise, the passage 580 communicates fluid between the fluid chamber 528 and the passage 556, such that the chamber 528 and passage 556 are at substantially the same pressure as one another. As appreciated, the piston 502 includes the seals 506 and 508 to isolate the fluid in the passage 556 from the fluid in the chamber 552. Accordingly, the fluids may be the same or different from one another. The piston 502 also moves along the axis 520 of the cylinder 504 to pressure balance the fluid in the passage 556 with the fluid in the chamber 552.

Thus, during an increase in pressure in the passage 556, the fluid passes through the passage 580 and into the fluid chamber 528, thereby biasing the piston 502 to move from the chamber 528 toward the chamber 526 until a pressure balance is reached between the chambers 526 and 528 (and thus between the passage 556 and chamber 552). Likewise, during a decrease in pressure in the passage 556, the fluid passes through the passage 578 and into the fluid chamber 526, thereby biasing the piston 502 to move from the chamber 526 toward the chamber 528 until a pressure balance is reached between the chambers 526 and 528 (and thus between the passage 556 and chamber 552). Finally, the pressure balance system 546 includes an electrical connection plug 576. The electrical connection plug 576 permits electrical communication between the transducers 566 and 568 and the controller 122, while maintaining a fluid tight seal under significant pressure.

Figure 11:
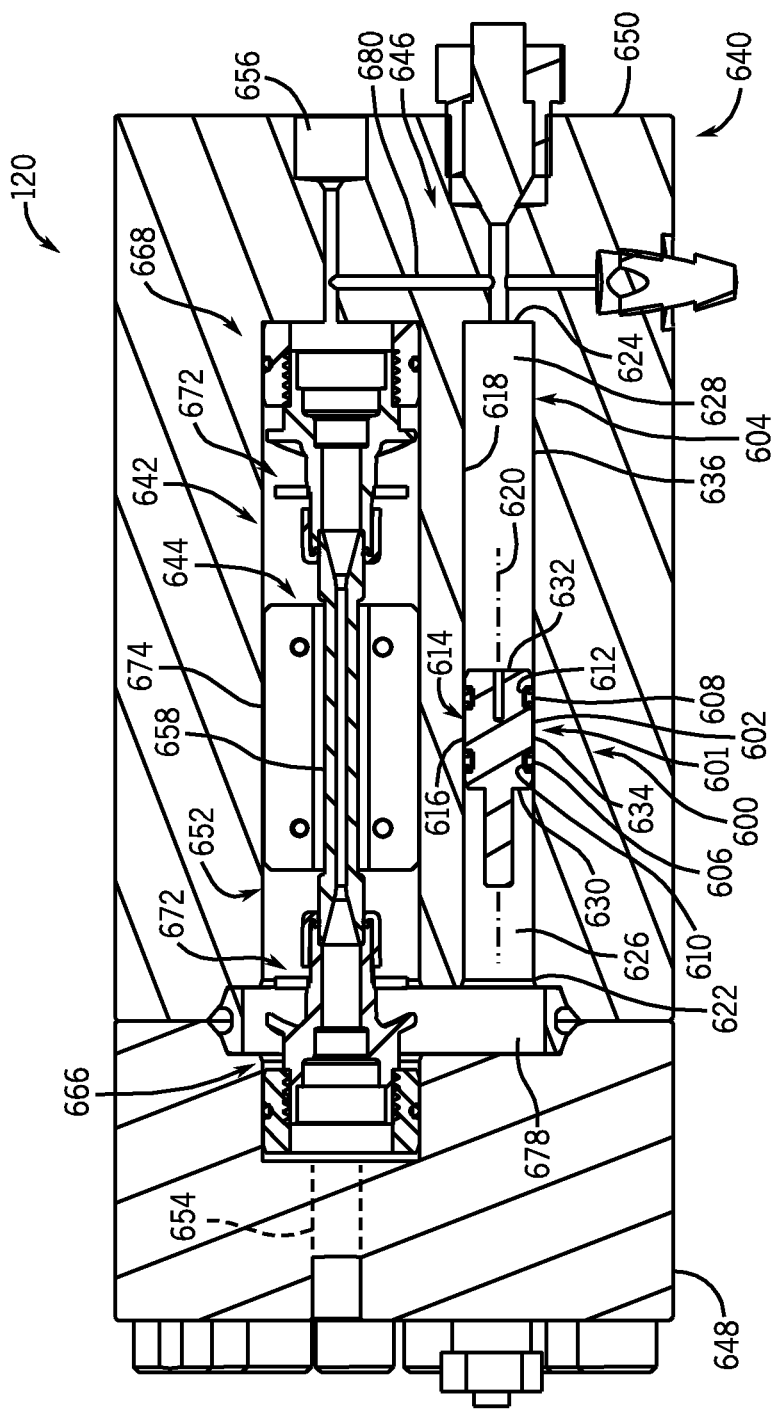
FIG. 11 is a cross-sectional view of an embodiment of a low flow ultrasonic flow meter with a pressure adjusting mechanism.

FIG. 11 is a cross-sectional side view of an embodiment of a low flow ultrasonic flow meter 120 with a pressure equalizing mechanism 600. For example, the pressure equalizing mechanism 600 may include a piston-cylinder assembly 601 having a piston 602 disposed in a cylinder 604. In the illustrated embodiment, the piston 602 includes one or more seals, such as first and second annular seals or rings 606 and 608, which are disposed in annular seal grooves 610 and 612, respectively. The piston 602 may be made of any suitable material, such as metal, plastic, ceramic, cermet, or any combination thereof. For example, the piston 602 may be made of a stainless steel. Furthermore, the seals 606 and 608 may be made from any suitable material, such as metal, plastic, fabric, or any combination thereof. In some embodiments, the piston 602 may exclude the seals 606 and 608 and associated seal grooves 610 and 612. Some embodiments also may employ a coating 614 disposed along an exterior surface 616 of the piston 602 and/or an interior surface 618 of the cylinder 604. The coating 614 may include a corrosion resistant coating, a wear resistant coating, a low friction coating, or any combination thereof. For example, the coating 614 may include a low friction coating, such as polytetrafluoroethylene (PTFE) or Teflon. By further example, the coating 614 may include a wear resistant coating, such as tungsten carbide.

In the illustrated embodiment, the piston 602 moves along an axis 620 of the cylinder 604 between opposite first and second ends 622 and 624 of the cylinder 604 in response to pressure changes between opposite first and second fluid chambers 626 and 628, respectively. In particular, the first fluid chamber 626 is defined between the first end 622 of the cylinder 604 and a first end 630 of the piston 602, while the second fluid chamber 628 is defined between the second end 624 of the cylinder 604 and a second end 632 of the piston 602. As the pressure changes in the first and second fluid chambers 626 and 628, the piston 602 moves along the axis 620 of the cylinder 604 to pressure balance the first and second fluid chambers 626 and 628. In the illustrated embodiment, the piston 602 has a cylindrical shaped body 634, which may be solid or hollow. Similarly, the cylinder 604 has a cylindrical shaped geometry 636 to accommodate the cylindrical shaped body 634 of the piston 602. However, other embodiments of the piston 602 and the cylinder 604 may have other geometrical shapes, such as oval, rectangular, polygonal, and so forth. Furthermore, some embodiments of the pressure equalizing mechanism 600 may include a plurality of pistons 602 disposed in the cylinder 604, or a plurality of piston-cylinder assemblies 601 each having at least one piston 602 disposed in a cylinder 604. In other embodiments, the piston 604 may be replaced with a bellows, diaphragm, or other pressure balancing mechanism in the cylinder 604. As discussed below, the piston-cylinder assembly 601 is configured to provide pressure balancing to increase the operational pressure range of the low flow ultrasonic flow meter 120.

In addition, the low flow ultrasonic flow meter 120 of FIG. 11 includes a housing 640, ultrasonic meter system 642, acoustic isolator system 644, and a pressure balance system 646. In the illustrated embodiment, the housing 640 includes a lid 648 that connects to a body portion 650. Together, the lid 648 and body portion 650 define a chamber 652. As illustrated, the lid 648 and the body portion 650 each define a passage that allows fluid to pass through the flow meter 120. Specifically, the lid 648 defines a first passage 654, while the body 650 defines a second passage 656. In one embodiment, the first passage 654 is an entrance passage while the second passage 656 is an exit passage. In another embodiment, the first passage 654 is an exit passage while the second passage 656 is an entrance passage. The passages 654 and 656 connect to a conduit 658.

As illustrated, the ultrasonic meter system 642 includes transducers 666 and 668 and associated electrical lines and controller, as discussed in detail above with reference to FIG. 10. The ultrasonic transducers 666 and 668 may send or receive ultrasonic waves to the opposite transducer through the fluid traveling in the conduit 658. The controller 122 receives the transmission and reception times of the ultrasonic waves from the transducers 666 and 668 through electrical lines, which it then uses to calculate the fluid speed in the conduit 658. As discussed above, the faster a fluid is traveling in the conduit 658 the faster a wave will travel from the upstream transducer 668 to the downstream transducer 666, or vice versa. Likewise, a fast moving fluid will slow a wave traveling against the current from the downstream transducer 666 to the upstream transducer 668, or vice versa. With this information, the controller 122 is able to determine the flow rate of the fluid by comparing the speed of the wave in the flow meter to a known speed of the wave in a motionless fluid.

As further illustrated in FIG. 11, the flow meter 120 includes the acoustic isolation system 644. The acoustic isolation system 644 uses acoustic isolation rings 672 to prevent the transducers 666 and 668 from communicating with each other except through the fluid traveling in conduit 658. For example, the acoustic isolation rings 672 may be made of an acoustic isolation material, such as PEEK, and thus the rings 672 may be described as PEEK rings 672. The acoustic isolation system 644 may advantageously allow for accurate measurement of flow rates as low as 0.03 liters/hour (e.g., 0.05, 1, 2, 3, 4, 6, 10, 15, or 20 liters/hour), and as high as 120 liters/hour. In the present embodiment, the acoustic isolation system 644 includes a third acoustic isolation ring 674 (e.g., a PEEK ring) for absorbing ultrasonic waves created by the transducer 666 and 668. The ring 674 is disposed axially between the transducers 666 and 668, such that it absorbs ultrasonic wave energy traveling through the conduit wall 664. While the present embodiments illustrate a single third ring 674, in other embodiments there may be more rings in-between the transducers 666 and 668. For example, there may be 1, 2, 3, 4, 6, 6, 7, 8, 9, or 10 rings in-between the transducers 666 and 668. Furthermore, each of these rings may vary in thickness and or type of absorbing material with respect to the other rings. In the present embodiment, the pressure equalizing mechanism 600 (e.g., piston-cylinder assembly 601) may permit a second fluid to occupy the chamber 652 surrounding the conduit 658 such that the second fluid is isolated from the first fluid flowing through the conduit 648.

The second fluid may be specifically selected based on acoustic damping properties, e.g., the second fluid may be a protective liquid that will not corrode the housing 640, the PEEK rings 672 and 674, or otherwise negatively affect the system. For example, the second fluid may include oil. In some embodiments, the second fluid may advantageously include fine particles that promote acoustic damping (e.g., sand, beads, foam, etc.).

The flow meter 120 may also include the pressure balance system 646. The pressure balance system 646 includes the chamber 652, conduit 658, and pressure equalizing mechanism 600 (e.g., piston-cylinder assembly 601). The pressure balance system 646 allows the ultrasonic meter system 642 to operate in pressure ranges between approximately 0 to 50,000 psi, while the flow rates may range between approximately 0.01 to 1000 liters/hour. For example, the flow meter may be configured to measure low flow rates less than approximately 0.01, 0.02, 0.03, 0.04, 0.05, 0.1, 0.2, 0.3, 0.4, 0.5, 0.6, 0.7, 0.8, 0.9, 1, 2, 3, 4, 5, 10, 15, 20, or 25 liters/hour, while operating under pressures up to or greater than 5,000 psi, 10,000 psi, 15,000 psi, 20,000 psi, 25,000 psi, 30,000 psi, 40,000 psi, or 50,000 psi.

In the illustrated embodiment, the pressure equalizing mechanism 600 (e.g., piston-cylinder assembly 601) is radially offset away from the fluid chamber 652, but connects both to the fluid chamber 652 and the fluid flow path through the flow meter 120. For example, the illustrated pressure equalizing mechanism 600 includes first and second conduits or passages 678 and 680, which couple to the first and second fluid chambers 626 and 628 of the cylinder 604. Thus, the passage 678 communicates fluid between the fluid chambers 626 and 652, such that the chambers 626 and 652 are at substantially the same pressure as one another. Likewise, the passage 680 communicates fluid between the fluid chamber 628 and the passage 656, such that the chamber 628 and passage 656 are at substantially the same pressure as one another. As appreciated, the piston 602 includes the seals 606 and 608 to isolate the fluid in the passage 656 from the fluid in the chamber 652. Accordingly, the fluids may be the same or different from one another. The piston 602 also moves along the axis 620 of the cylinder 604 to pressure balance the fluid in the passage 656 with the fluid in the chamber 652.

Thus, during an increase in pressure in the passage 656, the fluid passes through the passage 680 and into the fluid chamber 628, thereby biasing the piston 602 to move from the chamber 628 toward the chamber 626 until a pressure balance is reached between the chambers 626 and 628 (and thus between the passage 656 and chamber 652). Likewise, during a decrease in pressure in the passage 656, the fluid passes through the passage 678 and into the fluid chamber 626, thereby biasing the piston 602 to move from the chamber 626 toward the chamber 628 until a pressure balance is reached between the chambers 626 and 628 (and thus between the passage 656 and chamber 652).

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:
1. A system, comprising:
 a flow meter, comprising:
  a first flow sensor disposed about a fluid flow path; and a pressure balancing system configured to pressure balance the first flow sensor relative to a fluid flow along the fluid flow path.

2. The system of claim 1, wherein the pressure balancing system is configured to pressure balance the first flow sensor relative to the fluid flow up to a pressure of approximately 5,000 psi.

3. The system of claim 1, wherein the pressure balancing system is configured to pressure balance the first flow sensor relative to the fluid flow up to a pressure of approximately 10,000 psi.

4. The system of claim 1, wherein the pressure balancing system comprises a piston-cylinder assembly disposed along a fluid passage between the first flow sensor and the fluid flow path.

5. The system of claim 1, wherein the pressure balancing system comprises a bellows disposed along a fluid passage between the first flow sensor and the fluid flow path.

6. The system of claim 1, wherein the pressure balancing system comprises a fluid chamber, the first flow sensor is disposed in the fluid chamber, and the pressure balancing system is configured to pressure balance the fluid chamber with the fluid flow path.

7. The system of claim 6, wherein the pressure balancing system is configured to enable fluid communication between the fluid chamber and the fluid flow path.

8. The system of claim 6, wherein the pressure balancing system is configured to block fluid communication between the fluid chamber and the fluid flow path.

9. The system of claim 6, wherein the flow meter comprises:
a conduit disposed about the fluid flow path; and
a housing disposed about the conduit to define the fluid chamber about the conduit, wherein the first flow sensor is coupled to the conduit in the fluid chamber, and the pressure balancing system is configured to pressure balance the fluid chamber with the fluid flow path to reduce stress on the conduit.

10. The system of claim 6, comprising a second flow sensor disposed in the fluid chamber, wherein the first and second flow sensors are configured to communicate between one another.

11. The system of claim 1, comprising a mineral extraction system having the flow meter.

12. The system of claim 11, wherein the mineral extraction system comprises a chemical-injection management system having the flow meter.

13. The system of claim 1, comprising an underwater system having the flow meter.

14. A system, comprising:
an underwater apparatus; and
a meter coupled to the underwater apparatus, wherein the meter comprises:
a conduit;
a housing disposed about the conduit to define a pressurized fluid chamber about the conduit; and
a first sensor disposed in the pressurized fluid chamber.

15. The system of claim 14, wherein the pressurized fluid chamber is configured to at least substantially balance fluid pressure internal and external to the conduit via the pressurized fluid chamber.

16. The system of claim 14, comprising a passage extending between the pressurized fluid chamber and the conduit, wherein the passage is configured to enable fluid communication between the pressurized fluid chamber and the conduit.

17. The system of claim 14, comprising a pressure balancer disposed along a passage between the pressurized fluid chamber and the conduit, wherein the pressure balancer is configured to block fluid communication between the pressurized fluid chamber and the conduit, and the pressure balancer is configured to balance fluid pressure internal and external to the conduit by moving an element in response to a pressure differential between the pressurized fluid chamber and the conduit.

18. The system of claim 14, comprising a second sensor disposed in the pressurized fluid chamber, wherein the first and second sensors are configured to communicate between one another.

19. A system, comprising:
a meter, comprising:
a conduit disposed about a fluid flow path;
a first sensor coupled to the conduit, wherein the first sensor is configured to sense a first parameter of a fluid flow along the fluid flow path; and
a fluid chamber disposed about the conduit, wherein the fluid chamber is configured to at least substantially balance fluid pressure internal and external to the conduit.

20. The system of claim 19, wherein the meter comprises a second sensor coupled to the conduit.

21. The system of claim 1, wherein the first flow sensor extends completely around an outer circumference of the fluid flow path.

22. The system of claim 21, wherein the flow meter comprises a second flow sensor that extends completely around the outer circumference of the fluid flow path, wherein the first and second flow sensors are axially offset from one another along the fluid flow path.

23. The system of claim 22, wherein the first and second flow sensors are coupled to a conduit along a straight section of the conduit.

24. The system of claim 14, wherein the first sensor extends completely around an outer circumference of the conduit.

25. The system of claim 24, wherein the meter comprises a second sensor that extends completely around the outer circumference of the conduit, wherein the first and second sensors are axially offset from one another along the conduit.

26. The system of claim 25, wherein the first and second sensors are coupled to the conduit along a straight section of the conduit.

27. The system of claim 19, wherein the first sensor extends completely around an outer circumference of the conduit.

28. The system of claim 27, wherein the meter comprises a second sensor that extends completely around the outer circumference of the conduit, wherein the first and second sensors are axially offset from one another along the conduit.

* * * * *